US011692973B2

(12) United States Patent
Lee et al.

(10) Patent No.: US 11,692,973 B2
(45) Date of Patent: Jul. 4, 2023

(54) DETERMINATION OF RESERVOIR HETEROGENEITY

(71) Applicant: Saudi Arabian Oil Company, Dhahran (SA)

(72) Inventors: Ji Soo Lee, Katy, TX (US); Gary Eppler, Baytown, TX (US)

(73) Assignee: Saudi Arabian Oil Company, Dhahran (SA)

(*) Notice: Subject to any disclaimer, the term of this patent is extended or adjusted under 35 U.S.C. 154(b) by 363 days.

(21) Appl. No.: 17/140,230

(22) Filed: Jan. 4, 2021

(65) Prior Publication Data
US 2022/0214310 A1 Jul. 7, 2022

(51) Int. Cl.
*G01N 29/07* (2006.01)
*E21B 49/02* (2006.01)
(Continued)

(52) U.S. Cl.
CPC ............ *G01N 29/07* (2013.01); *E21B 49/02* (2013.01); *G01N 33/24* (2013.01); *G01V 99/00* (2013.01); *G01N 2291/011* (2013.01); *G01N 2291/023* (2013.01); *G01N 2291/048* (2013.01); *G01N 2291/10* (2013.01)

(58) Field of Classification Search
CPC .. G01N 29/07; G01N 33/24; G01N 2291/011; G01N 2291/023; G01N 2291/048; G01N 2291/10; G01N 29/27; G01N 2291/0232; G01N 2291/02458; G01N 2291/02491; G01N 2291/0289; G01N 2291/102; G01N 2291/2634; G01N 2210/6222; G01N 2210/624;
(Continued)

(56) References Cited

U.S. PATENT DOCUMENTS

| 4,631,963 | A | 12/1986 | Sprunt et al. |
| 5,109,697 | A | 5/1992 | Millheim |

(Continued)

FOREIGN PATENT DOCUMENTS

| EP | 0466384 | * | 2/1991 |
| WO | WO-2017204689 A1 | * | 11/2017 |

OTHER PUBLICATIONS

Lee, "Ultrasonic test redesigns sample geometries, identifies high-resolution anisotropy in shale." Oil & Gas Journal, October 201, 42-47, 6 pages.
(Continued)

*Primary Examiner* — Jacques M Saint Surin
(74) *Attorney, Agent, or Firm* — Fish & Richardson P.C.

(57) ABSTRACT

Methods for determining reservoir characteristics of a well can include receiving a first core from the well; performing an experiment to determine the wave velocity associated with a first direction of the first core, the experiment including: transmitting an ultrasonic wave through the first core in the first direction; receiving the transmitted ultrasonic wave; and determining a directional wave velocity of the first core based on the transmitted ultrasonic wave and the received transmitted ultrasonic wave, wherein the directional wave velocity represents a wave velocity along the first direction; rotating the first core about a longitudinal axis of the first core; and performing the experiment along a second direction of the first core.

20 Claims, 22 Drawing Sheets

(51) Int. Cl.
*G01N 33/24* (2006.01)
*G01V 99/00* (2009.01)

(58) Field of Classification Search
CPC ... G01N 2210/626; E21B 49/02; E21B 47/00; G01V 99/00; G01H 5/00
USPC .......................................................... 73/597
See application file for complete search history.

(56) References Cited

U.S. PATENT DOCUMENTS

| | | | |
|---|---|---|---|
| 5,134,271 | A | 7/1992 | Sondergeld et al. |
| 5,178,005 | A | 1/1993 | Peterson et al. |
| 8,619,501 | B2 * | 12/2013 | Garcia-Osuna ........ G01N 29/07 73/152.11 |
| 9,464,523 | B1 * | 10/2016 | Grove .................. G01N 15/082 |
| 9,897,428 | B2 * | 2/2018 | Hieb ........................ G01B 5/10 |
| 10,345,269 | B2 | 7/2019 | Lee et al. |
| 10,983,038 | B2 * | 4/2021 | Manning ................. E21B 49/08 |
| 11,579,333 | B2 * | 2/2023 | Almarzooq ............. E21B 49/02 |
| 2013/0274149 | A1 | 10/2013 | Lafitte et al. |
| 2016/0109603 | A1 | 4/2016 | Jin et al. |
| 2017/0241260 | A1 | 8/2017 | Gonzalez et al. |
| 2018/0155615 | A1 | 6/2018 | Rahy et al. |
| 2019/0017203 | A1 | 1/2019 | Andoh et al. |

OTHER PUBLICATIONS

Sheriff, "Encyclopedic dictionary of applied geophysics." Geophysical References Series 13, Society of Exploration Geophysicists (SEG), 2001, 442 pages.
Thomsen, "Understanding seismic anisotropy in exploration and exploitation." SEG-European Association of Geoscientists and Engineers (EAGE) Distinguished Instructor Series 5, 2001, 305 pages.
Winn, "Log interpretation in heterogeneous carbonate reservoirs." SPE-818-G Petroleum Transactions, AIME, p. 268-274. T.P. 4637. Originally presented at Permian Basin Oil Recovery Conference, April 18-19, Midland, TX. SPE-818-G G, 1957, 268-274, 7 pages.
Sarout et al., "Anisotropy of elastic wave velocities in deformed shales: Part 1—Experimental results." Geophysics 73.5, Sep.-Oct. 2008, D75-D89, 15 pages.
PCT International Search Report and Written Opinion in International Appln. No. PCT/US2022/011067, dated Apr. 26, 2022, 16 pages.

* cited by examiner

DETERMINATION OF RESERVOIR HETEROGENEITY

TECHNICAL FIELD

This disclosure relates to a determination of reservoir heterogeneity, particularly using high-resolution primary wave velocity measurement at laboratory scale.

BACKGROUND

Unconventional rocks such as shale include various geologic features of faults, bedding planes, fractures, cracks, and laminations at various scales. Unlike conventional source rocks which exhibit approximately isotropic and homogeneous properties, unconventional source rocks can be both anisotropic and heterogeneous. For example, some unconventional rocks include different types and distributions of mineral compositions and rock matrices and some have physical and mechanical properties that depend on direction.

Determining the directional properties of unconventional rocks is a challenge. In some cases, seismic profiling or surveying can be used to determine these properties, but seismic profiling is expensive and is limited to a direction parallel to gravity from the Earth's surface. Seismic profiling is not an appropriate method for determining rock properties along a direction parallel to the Earth's surface. In some cases, injection pressure monitoring can be used to determine these properties along the direction parallel to Earth's surface, but the cost of this procedure is dependent on depth which tends to limit the procedure to shallow depths.

SUMMARY

Knowledge of reservoir characteristics at downhole conditions are used for oil and gas operations. Understanding the reservoir characteristics aid in the explorations, drilling optimizations, horizontal drilling optimizations, formation evaluations, perforation tunnel designs, reservoir navigations, hydraulic fracturing designs, and well completions. The reservoir characteristics are inferred by knowing physical and mechanical properties of the rocks that are part of the reservoir. For example, a direction parallel to a discontinuity in the rock is associated with a fast wave velocity, while a direction perpendicular to the discontinuity is associated with a slow wave velocity. The wave velocities of the rocks that make up the reservoir can be used to build a map of the discontinuities of the reservoir.

Knowledge of these wave speed differences is an indication of rock anisotropy and can be used on a larger scale to understand the regional tectonic stress differences related to plate tectonics as the minerals of the rock record the strain from the stress applied. In petroleum applications, stress differences could be used to compute a maximum and minimum horizontal stress to ensure a horizontal well is drilled in the direction of minimum horizontal stress. This is important because, when completing the well from hydraulic fracturing the, fractures will propagate orthogonally to the wellbore axis which will access more reservoir volume. The stress differences also can be used to assess wellbore stability issues. For example, when drilling vertical wells, any regional stress anisotropy can create well bore breakout in the direction of the minimum horizontal stress which can affect the geometry of the wellbore. Severe breakout can cause loss of the well and increases the rugosity of the hole.

This specification describes methods for determining the physical and mechanical properties of rocks from core samples, for example core samples from an unconventional source rock reservoir. In some cases, the orientations of maximum and minimum primary (P) wave velocities and the orientations of normalized P waves for each core sample are determined. When multiple core samples are extracted at depth intervals and tested, the resulting wave velocities infer directional information of heterogeneity and anisotropy as a function of depth in the reservoir.

The systems and methods described in this specification provide various advantages.

The method is non-destructive so that the core samples can be used for other testing purposes or preserved after the testing is complete.

The method is scalable to an arbitrary number of wave velocity measurements along the circumference so that the test can be tailored to balance testing time with result resolution.

The method is fast and cost effective so that multiple core samples can be tested daily.

The method provides high-resolution and reliable accuracy.

For ease of description, terms such as "upper", "lower", "top", "bottom" "left" and "right" are relative to the orientation of the features in the figures rather than implying an absolute direction.

The details of one or more embodiments of these systems and methods are set forth in the accompanying drawings and the description to be presented. Other features, objects, and advantages of these systems and methods will be apparent from the description and drawings, and from the claims.

DESCRIPTION OF DRAWINGS

Like reference symbols in the various drawings indicate like elements.

DETAILED DESCRIPTION

This specification describes systems and methods for determining the physical and mechanical properties of rocks from core samples, for example core samples from an unconventional source rock reservoir. In some cases, the orientations of maximum and minimum primary (P) wave velocities and the orientations of normalized P waves for each core sample are determined. When multiple core samples are extracted at depth intervals and tested, the resulting wave velocities provide directional information of heterogeneity and anisotropy as a function of depth in the reservoir.

Figure 1:
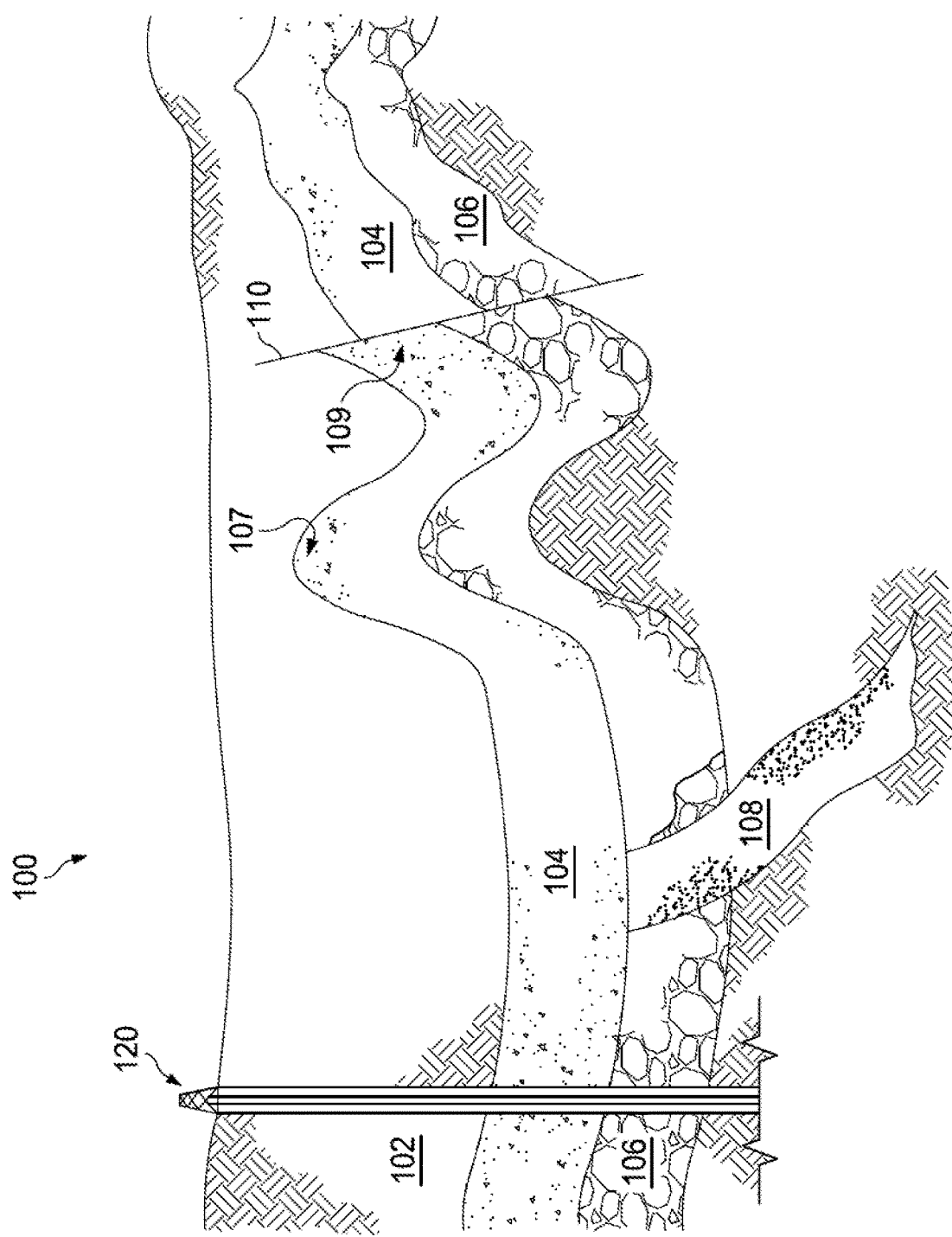
FIG. 1 is a schematic view of subterranean features such as facies and faults.

FIG. 1 is a schematic view of subterranean features such as facies and faults in a subterranean formation 100. When a well 120 is drilled into the subterranean formation 100, cylindrical core samples can be extracted in depth intervals and are tested to determine the reservoir properties in the vicinity of the well 120. The reservoir properties are inferred from the wave velocity testing described in this specification. Once the well 120 is complete, it can be used to extract oil and gas from the subterranean formation 100.

The subterranean formation 100 includes a layer of impermeable cap rock 102 at the surface. Facies underlying the impermeable cap rocks 102 include a sandstone layer 104, a limestone layer 106, and a sand layer 108. A fault line 110 extends across the sandstone layer 104 and the limestone layer 106. In some cases, layers 104, 106, and 108 include unconventional rocks.

Oil and gas tend to rise through permeable reservoir rock until further upward migration is blocked, for example, by the layer of impermeable cap rock 102. The directional wave velocity information is used to identify locations where interaction between layers of the subterranean formation 100 are likely to trap oil and gas by limiting this upward migration. For example, FIG. 1 shows an anticline trap 107, where the layer of impermeable cap rock 102 has an upward convex configuration, and a fault trap 109, where the fault line 110 might allow oil and gas to flow in with clay material between the walls traps the petroleum. Other traps include salt domes and stratigraphic traps.

Different geologic bodies or layers in the earth are distinguishable because the layers have different wave velocity properties and directionality dependence of the wave velocities. For example, in the subterranean formation 100, the velocity of waves traveling through the subterranean formation 100 will be different in the sandstone layer 104, the limestone layer 106, and the sand layer 108. If a core sample was extracted in a layer that is made of unconventional rock, the wave velocity testing of the core sample would indicate the wave velocity directionality associated with the unconventional rock.

Figure 2A:
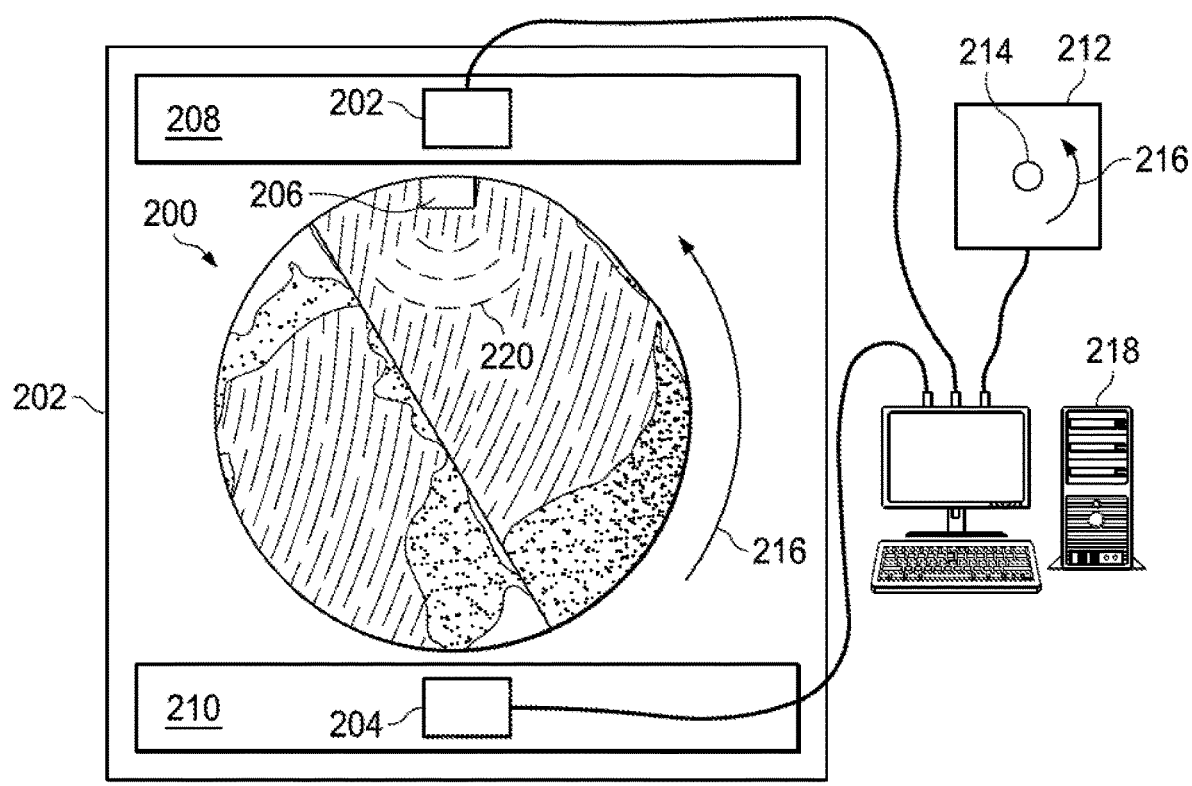
FIG. 2A is a testing machine for measuring the wave velocity directionality of a core.

FIG. 2A is a 4-inch diameter cylindrical core 200 extracted from an unconventional source rock reservoir and is a fine grain organic laminated rock. The cylindrical core 200 is placed in a testing machine 202.

It is preferable to use the larger 4-inch core opposed to a smaller core sample since the larger samples represent the macroscopic behavior of the core and reservoir better than smaller samples. However, in some cases, 2-inch diameter or smaller core samples are used. The core 200 includes an orientation marking 206 (shown facing the first ultrasonic transducer 202) so the orientation can be mapped to the resulting wave velocity data. The orientation marking 206 indicates the 0 degree increment. This represents where the wave velocity measurements should begin.

The testing machine 202 includes a pair of ultrasonic transducers 202, 204 placed on opposite sides 208, 210 of the core 200. Each side 208, 210 is fixed to the testing machine 202. The first ultrasonic transducer is configured to transmit an ultrasonic wave 220 that passes through the core 200 and reaches the second ultrasonic transducer 204. The ultrasonic transducers 202, 204 located on either side of the core 200 are automatically applied to the cylindrical outer surface of the core 200 briefly to take a measurement and then are retracted afterward so that the core can then be rotated automatically to the next azimuth for the next measurement. A processor 218 of the testing machine 218 controls actuators to move the ultrasonic transducers 202, 204 to and from the cylindrical outer surface of the core 200.

Figure 2B:
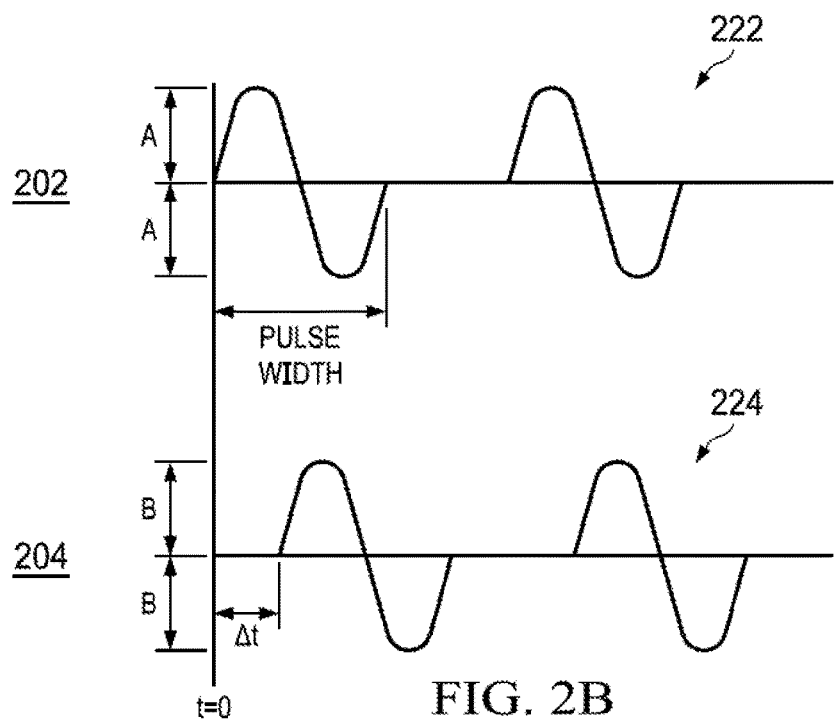
FIG. 2B is example signals transmitted and received by the ultrasonic transducers of the testing machine of FIG. 2A.

FIG. 2B is a signal 222 transmitted by the first ultrasonic transducer 202 (top) and a signal 224 received by the second ultrasonic transducer 204 (bottom). The signal 224 is offset in time relative to the signal 222 representative of the time of flight of the wave 220. In some testing machines, an amplitude A, B, associated with each signal 222, 224, respectively, is used to determine loss of the wave 220 as it travels through the core 200.

The processor 218 of the testing machine 202 compares the signal 224 from the second ultrasonic transducer 204 with the signal 222 of the first ultrasonic transducer 202 to determine the time of flight of the ultrasonic wave 220. In other words, the acoustic transducer 202 introduces an acoustic pulse which is then registered by the acoustic transducer 204 after having traveled through the diameter of the core 200. The diameter of the core 200 is measured and entered into the computer prior to measurement. The velocity is determined by dividing the distance that the pulse travels with respect to the diameter of the core 200, by the corresponding elapsed time for the acoustic pulse to travel to the acoustic transducer 204.

In some testing machines, the signal and pulse width is varied. In some testing machines, more than one pulse is transmitted to generate an average wave velocity through the core 200. For example, FIG. 2B shows a signal 222 with two pulses that have been transmitted by the first ultrasonic transducer 202. If the time of flight for each of these pulses varies, the processor 218 is configured to determine an average wave velocity. The processor 218 determines the wave velocity from the time of flight and the distance between the ultrasonic transducers 202, 204.

Once the ultrasonic signals 222, 224 are received by the processor 218, the processor 218 instructs an actuator 212 to rotate the core 200 about an axis 214 in the counterclockwise direction 216 as shown. This process rotates the core 200 in a 10-degree azimuth angle increment and is performed automatically by the processor 218 according to the input of the azimuth angle that is desired. However, in some cases, other increments and directions are used. For example, some testing machines use a 2-degree increment. In some testing machines, a 45-degree increment is used. The incremental rotation is user controllable to balance a testing time of the core sample with the amount of directional information desired from the test. In some testing machines, the core 200 rotates clockwise.

Figure 2C:
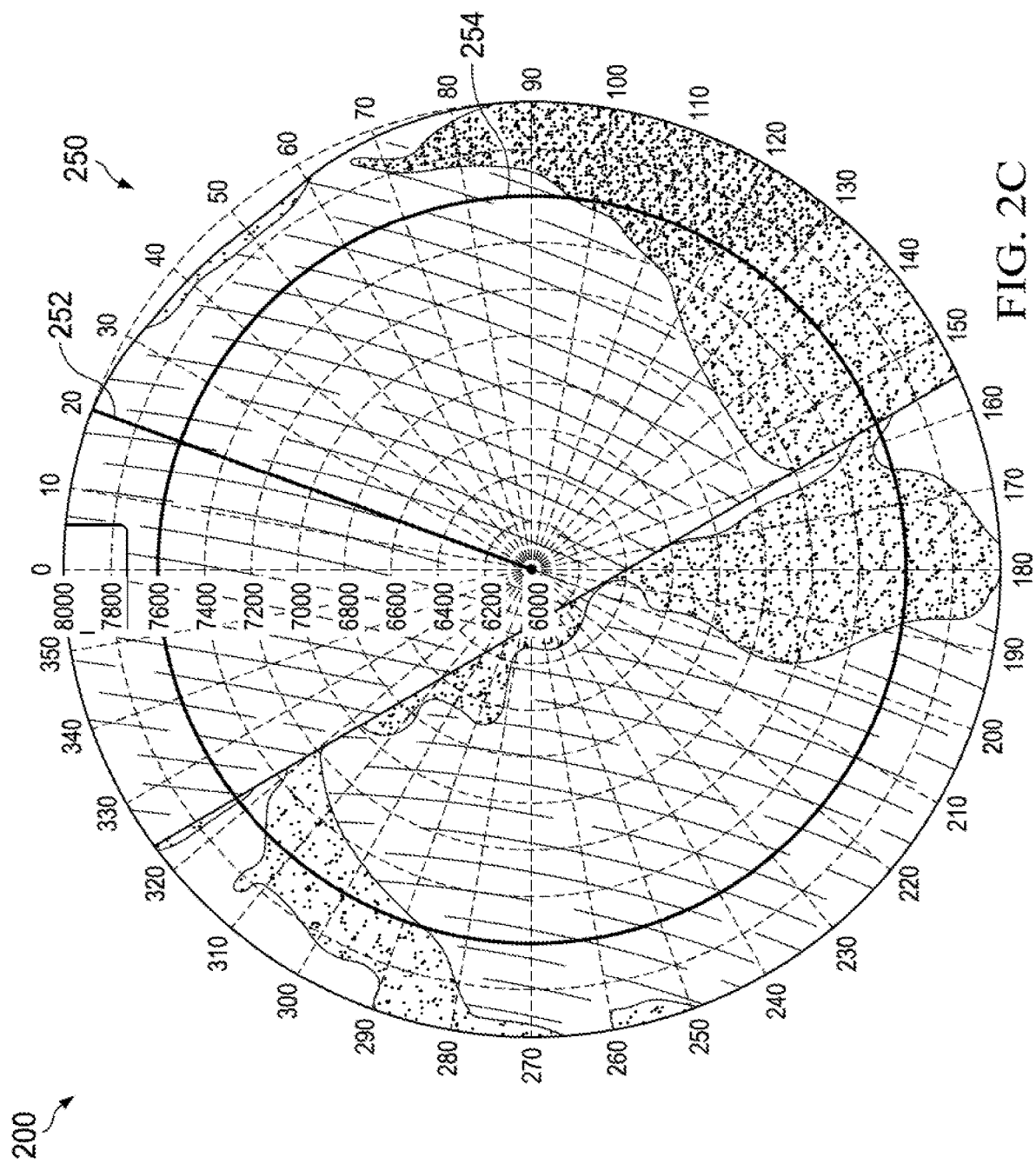
FIG. 2C is a template for the superposition of the wave velocity results from the testing machine with the physical geometry of the core.

FIG. 2C is a template of a 360-degree stereo net projection 250 superimposed on the core 200. The core 200 is seen along with a polar coordinate frame of the 360 degree stereo net projection 250. Each radial line 252 of the polar coordinate frame is oriented in 10 degree increments corresponding to the angle associated with the wave velocity measurements. Each circumferential "ring" about the center corresponds to the magnitude of the velocity (or speed) of the wave through the core 200 along the corresponding direction. When the results are plotted by the processor 218 on an image representing FIG. 2C as shown, the velocity magnitude and directionality along with the actual geometry of the core 200 is readily apparent.

Figure 3A:
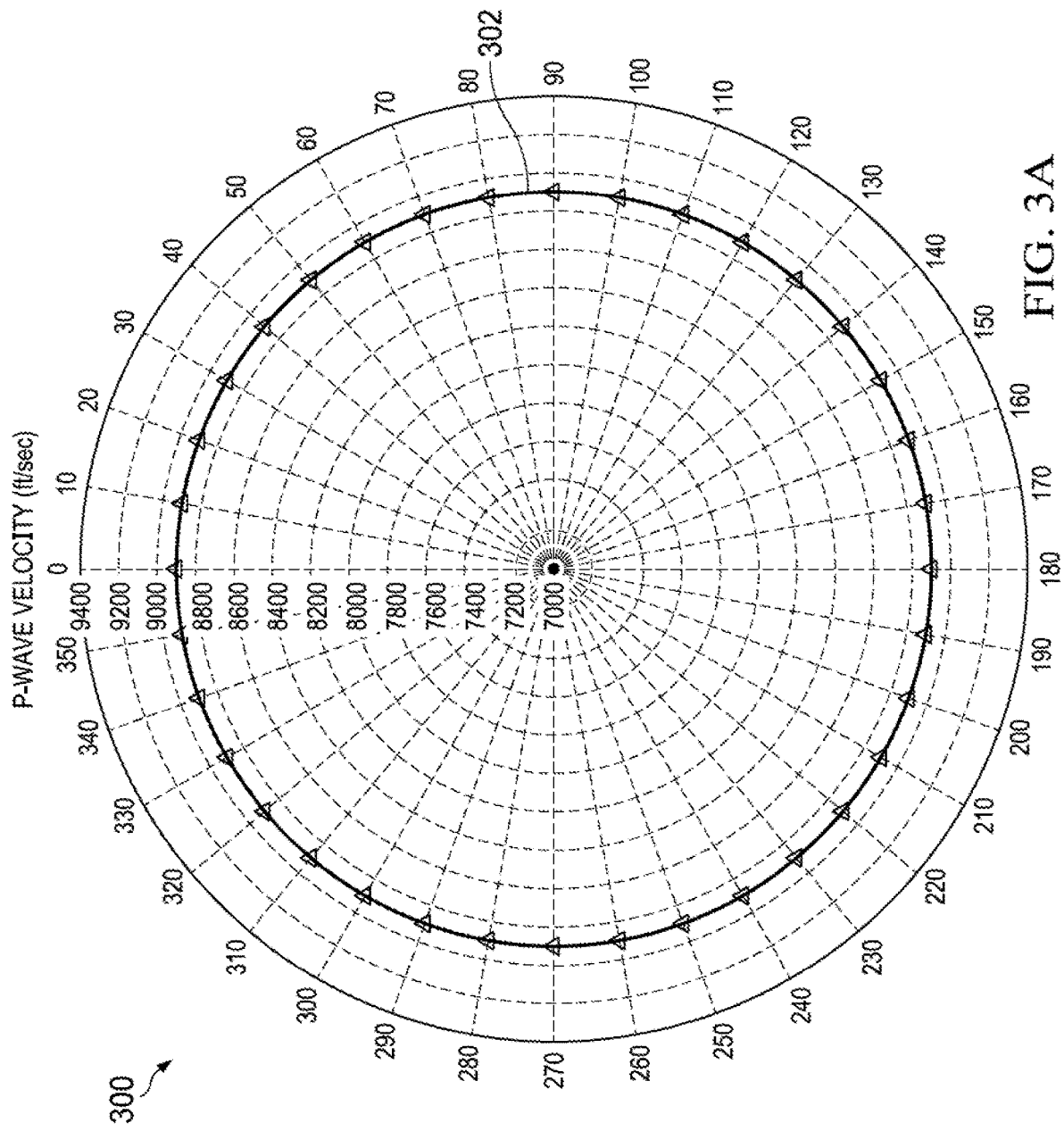
FIG. 3A is a template of P-wave velocity.
Figure 3B:
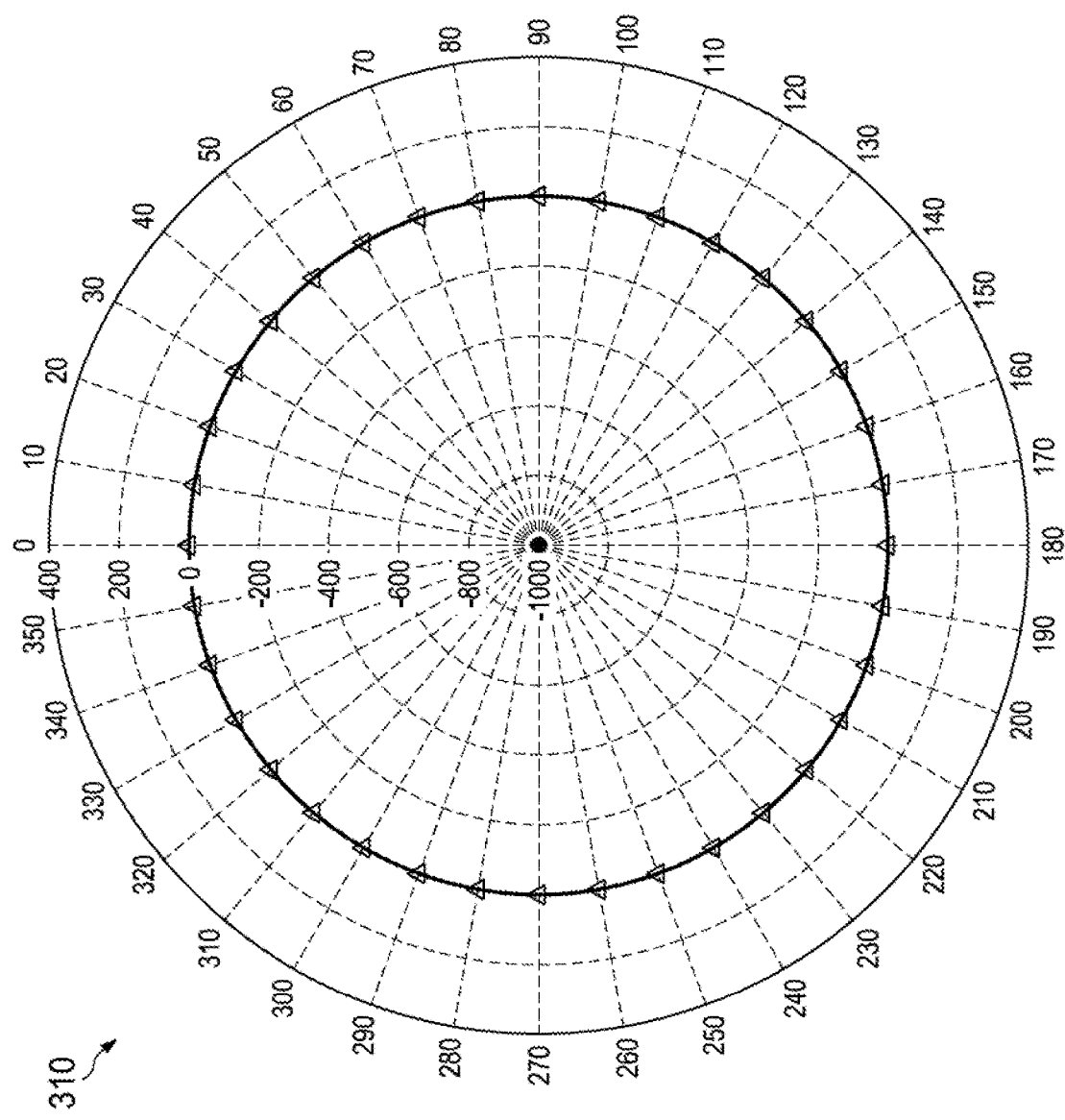
FIG. 3B is a template of a normalized P-wave velocity.

FIG. 3A is a template of P-wave velocity 300 in ft/sec and FIG. 3B is a template of a normalized P-wave velocity 310. The template indicates whether a stress anisotropy in the rock exists for each of the azimuth angles measured. Maximum p-wave or compressional velocity implies that the core the acoustic wave travelled through the core the fastest in the direction denoted by the azimuth angle. Conversely, the minimum p-wave velocity implies the p-wave travelled the slowest in the direction denoted by the azimuth angle. In some cases, the stress anisotropy is caused by geometric and orientation differences of the grains composing the rock due to differences in an applied stress.

The figures are generated by the processor 218 of the testing machine 202. In some cases, the figures are generated in spreadsheet software such as Microsoft EXCEL. The data points 302 are associated with a specific rotation of the core. For example, data point 302 indicates that the P-wave velocity is about 8900 ft/sec along a 20 degree orientation. The normalized P-wave velocity stereo net is plotted with the difference of each directional wave velocity minus the minimum wave velocity. In most cases, the normalized P-wave velocity results illustrates the directional anisotropy and/or heterogeneity along a certain direction within the core 200. However, in some testing machines, other quantities of interest are plotted. For example, in some testing machines, the normalized P-wave velocity stereo net is plotted based on each directional wave velocity minus the maximum wave velocity. In some testing machines, the normalized P-wave velocity stereo net is plotted based on each directional wave velocity divided by the maximum or minimum wave velocity.

The normalized P-wave velocity measurements are plotted using the processor 218 for each angular increment. Each angular increment assesses the rotation of reservoir heterogeneity in the source rock structure. This process indicates the directional orientation of the maximum and minimum P-wave velocities in each core. In addition, this procedure quantifies the reservoir heterogeneity along a particular direction in terms of the ratio between the maximum and minimum velocity difference. By testing multiple cores along a depth interval of a well, a map or pattern of the downhole condition in the unconventional source rock is revealed. The map or pattern is created by using computational software to plot the difference in velocities according to the value measured per the azimuth increment used. These maps or patterns are created according to the specific azimuth angle determined prior to the measurement.

Figure 4:
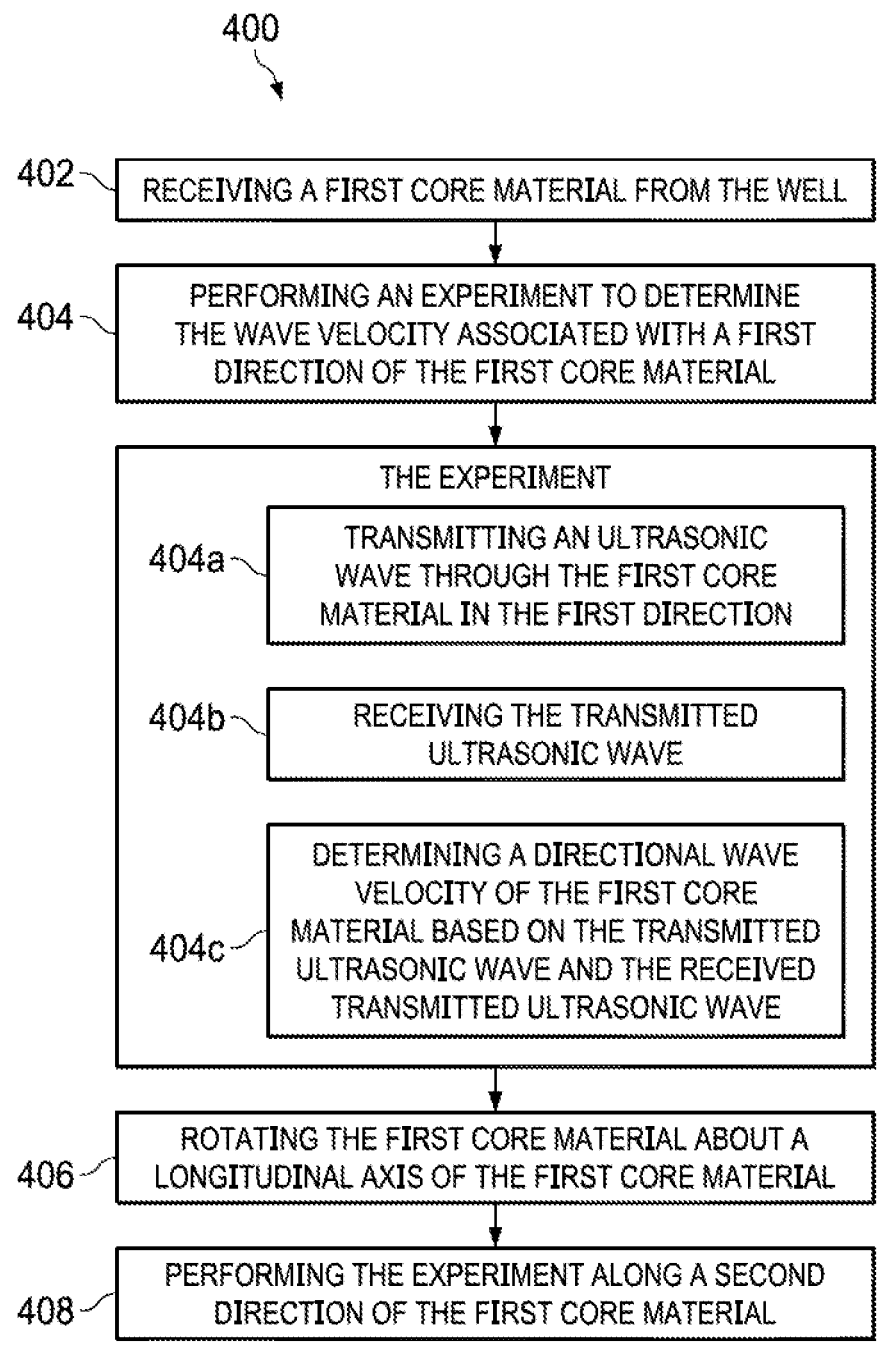
FIG. 4 is a flow diagram of a method for determining reservoir heterogeneity.
Figure 5:
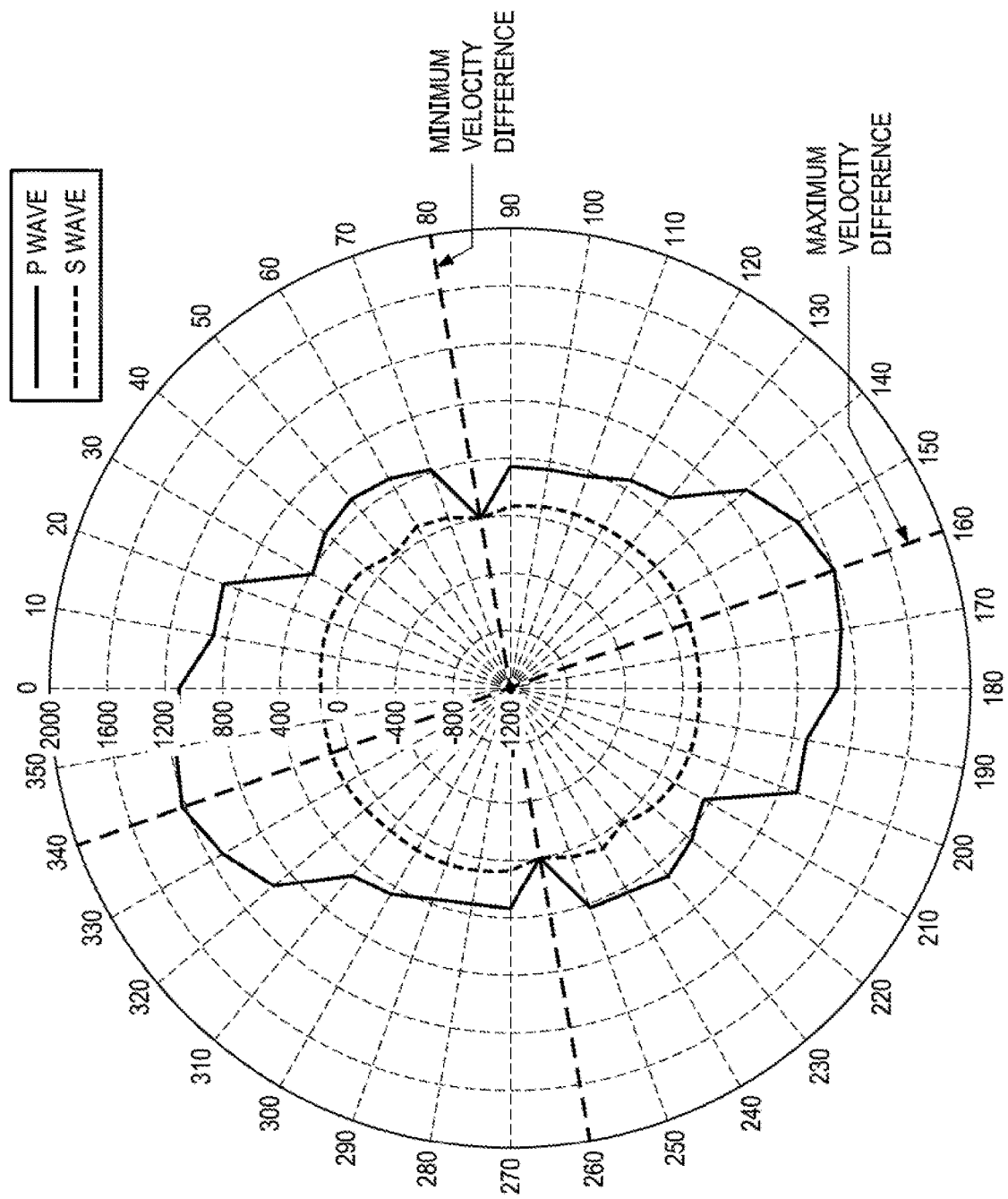
FIGS. 5-19 are plots of normalized radial acoustic heterogeneity for primary (P) and secondary (S) waves measured from the full-diameter core samples.

FIG. 4 is a flowchart of the method 400 performed by the testing machine 202.

Multiple whole cores are extracted from a well and prepared for testing. This includes receiving a first core from the well (step 402). For example, in some cases, 10 cores with a 4 inch diameter are extracted where each core represents a 100 ft depth increment. In some cases, the number of cores depends on the differences in the p-wave velocity to verify the p-wave velocity is either constant with depth or changes with depth. In some cases, the number of cores depends on thickness of the core. The preparing process involves cleaning the surface of the cores by sanding and/or polishing and measuring physical properties of the core. A marking is created on the core denoting the zero-angle position as shown in FIG. 2A and the core is placed into the testing machine 202 (also known as a radial acoustic scanning device) and oriented so the zero-degree reference position is aligned with the ultrasonic transducers 202, 204.

An experiment is performed to determine the wave velocity associated with a first direction of the first core (step 404). The experiment includes transmitting an ultrasonic signal from an ultrasonic transducer 202 which propagates through the first core in a first direction (step 404a) and is received by the ultrasonic transducer 204 (step 404b). The p-wave velocity is computed by the processor 218 using the arrival time of the signal of the ultrasonic transducer 204, the time of flight of the ultrasonic wave, and the distance traveled by the ultrasonic wave (step 404c). The maximum velocity difference and the minimum velocity difference are computed. The maximum velocity difference is determined by the difference of each directional wave velocity minus the maximum wave velocity of all wave velocities associated with the core. The minimum velocity difference is determined by the difference of each directional wave velocity minus the minimum wave velocity of all wave velocities associated with the first core.

The first core is rotated (e.g., either 10 degree clockwise or 10 degrees counterclockwise) about a longitudinal axis of the first core (step 406). The rotational direction preferably remains consistent throughout the testing procedure, however this is not required. The testing is repeated and a P-wave velocity along the 10 degree increment direction is determined based on the arrival time of the ultrasonic wave (step 408).

The test determines the wave velocity through the entire cross section of the core so only half of the possible rotations provide unique results. The testing machine measures the round-trip P-wave and takes the average so performing the test for the full 360 degree rotation is redundant. This process is preferably repeated for the unique 180 degree.

In other words, the round trip is used because the two ultrasonic transducers 202, 204 are aligned diametrically opposite from each other (at an angle of 180 degrees). A measurement taken at zero degrees will be the same as a measurement at 180 degrees. Likewise, if the measurement is taken at 90 degrees then the same value would be measured at 270 degrees. As a result, it is redundant to measure the full 360 degrees. For example, once the lower angle measurements from 0 to 180 degrees are taken, they can be copied/mirrored/extrapolated to the full 360 degrees. However, in some cases, the full 360 degrees is measured and the pairs or results (e.g., 0 degrees and 180 degree, 90 degrees and 270 degrees, etc.) are averaged.

After completion of velocity test, the velocity data is loaded into a spreadsheet such as Microsoft EXCEL. The P-wave velocity and normalized P-wave velocity are plotted. The normalized P-wave velocity is the P-wave velocity at each orientation (for example, 0 degrees, 10 degrees, 20 degrees, etc.). The user can place each arrow to indicate the fastest P-wave velocity direction and the slowest P-wave velocity direction. Indication of fastest P-wave velocity direction compared to the slowest P-wave velocity direction is a measure of the stress anisotropy in the core.

FIGS. 5-19 are plots of normalized radial acoustic heterogeneity for primary (P) and secondary (S) waves measured from the full-diameter core samples extracted from a single well. The results of FIGS. 5-19 show the velocity differences that occur according to differences in stress anisotropy. This approach focuses on P-waves because S-waves do not induce a change in particle volume in the rock like the p-waves. S-waves promotes bending of particles which could cause issues with interpreting arrival times of acoustic pulses with respect to organic matter. The bitumen present in the rock could also introduce uncertainty in the s-wave measurement because of a difference when propagating through the liquid. Since S-waves are not sensitive to the acoustic heterogeneity and they normally distribute as uniform, this invention focuses on P-waves. In general, the maximum and minimum P-wave velocity orientations are approximately perpendicular. This perpendicularity means that the maximum stress orientation experienced by the core is perpendicular to the least stressed region.

Sometimes, the cores are inadvertently cracked which are not part of the subsurface normally. Cracked cores can cause errors in velocities, introducing increased anisotropy in the rock measurement. This is especially relevant when the anisotropy measurement is made parallel to sediment bedding where organic matter can cause rock layers to spall and create void spaces. Since the P-waves propagate parallel to bedding with this instrument, those void spaces in the vertical core would have been affected by the resulting velocities.

Figure 6:
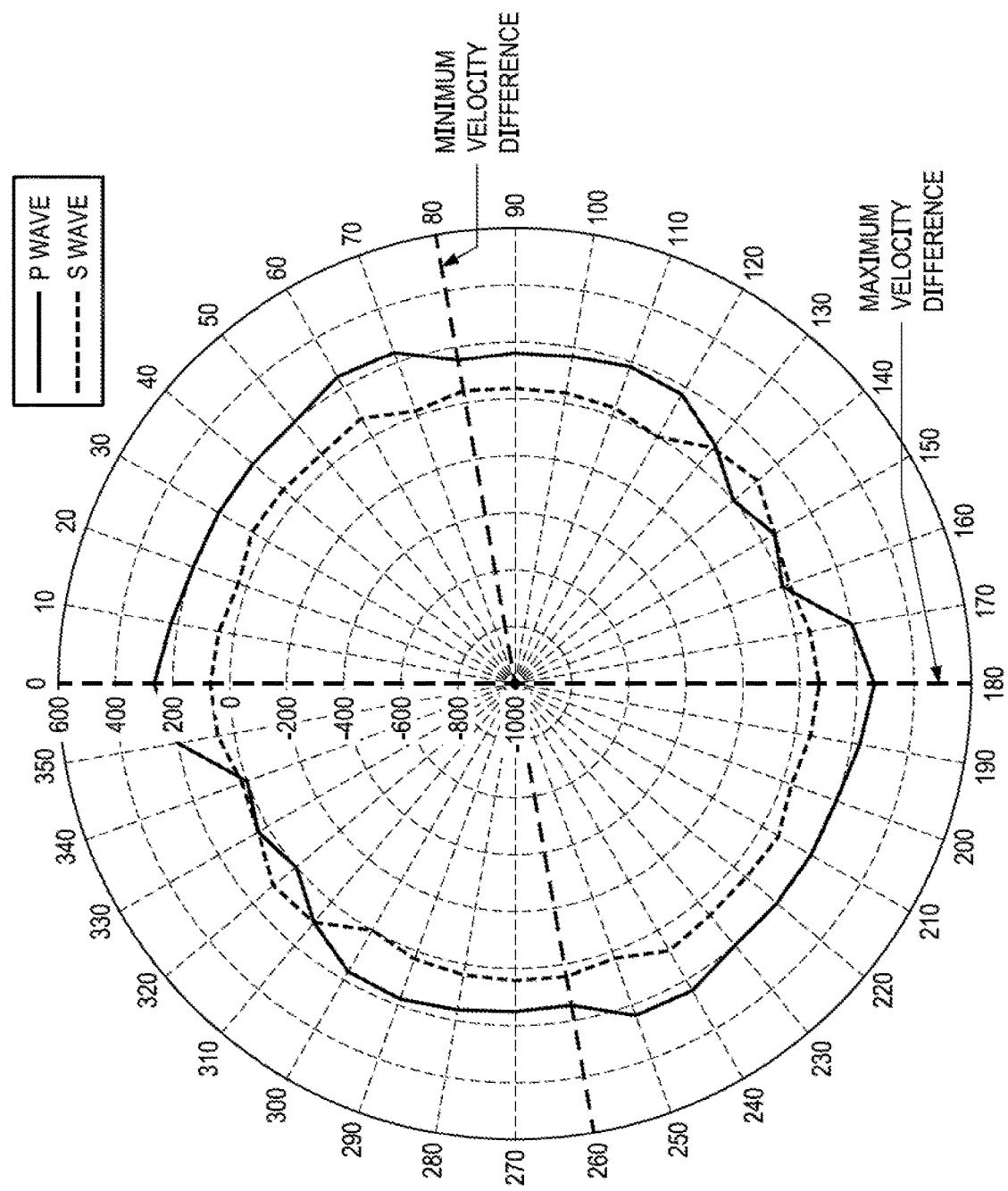

FIG. 6 plots the maximum P-wave orientation along N0° E or N0° W from sample #3.

Figure 7:
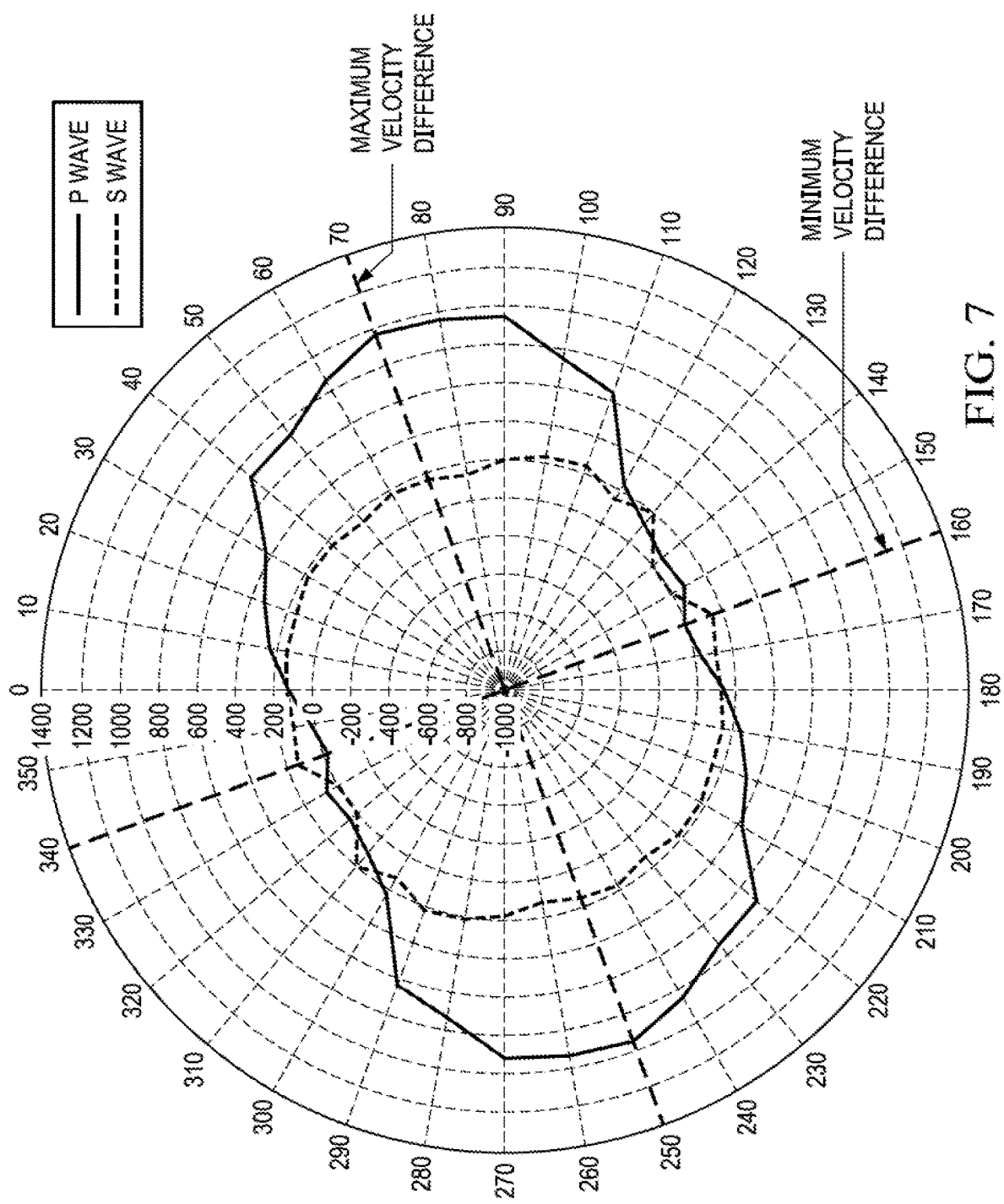

FIG. 7 plots the maximum P-wave orientation along N70° E from sample #4.

Figure 8:
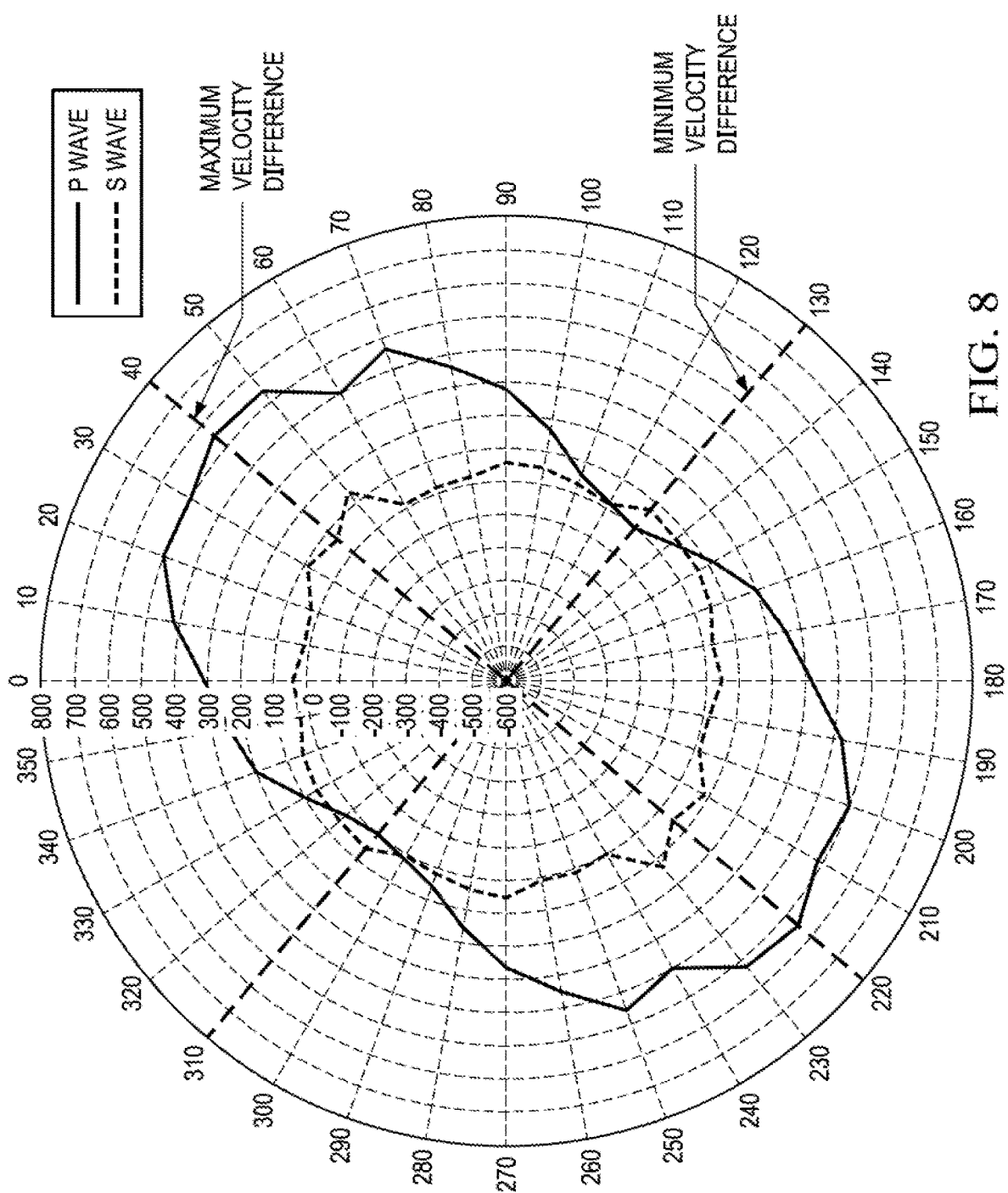

FIG. 8 plots the maximum P-wave orientation along N40° E from sample #5.

Figure 9:
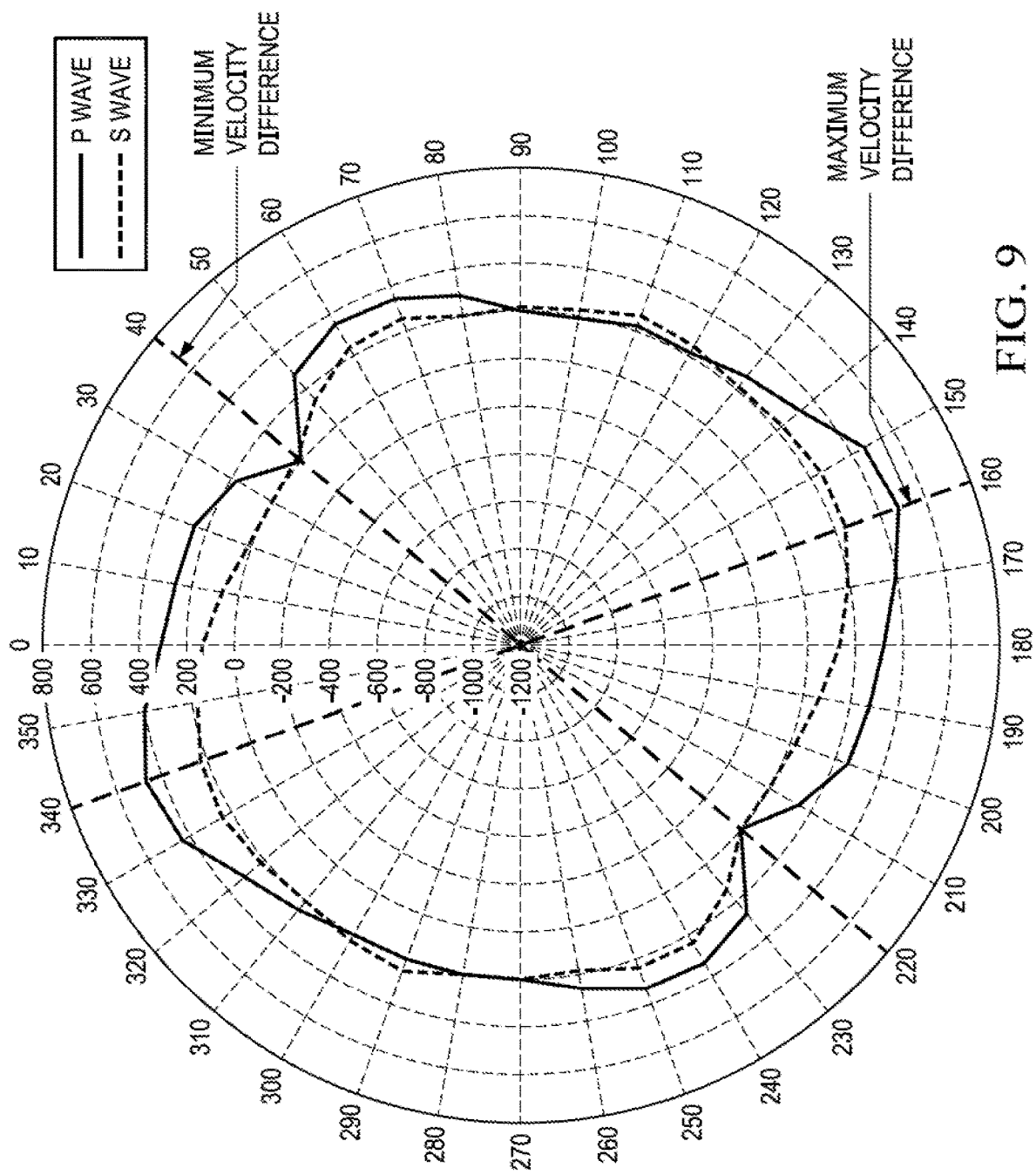

FIG. 9 plots the maximum P-wave orientation along N20° W from sample #7.

Figure 10:
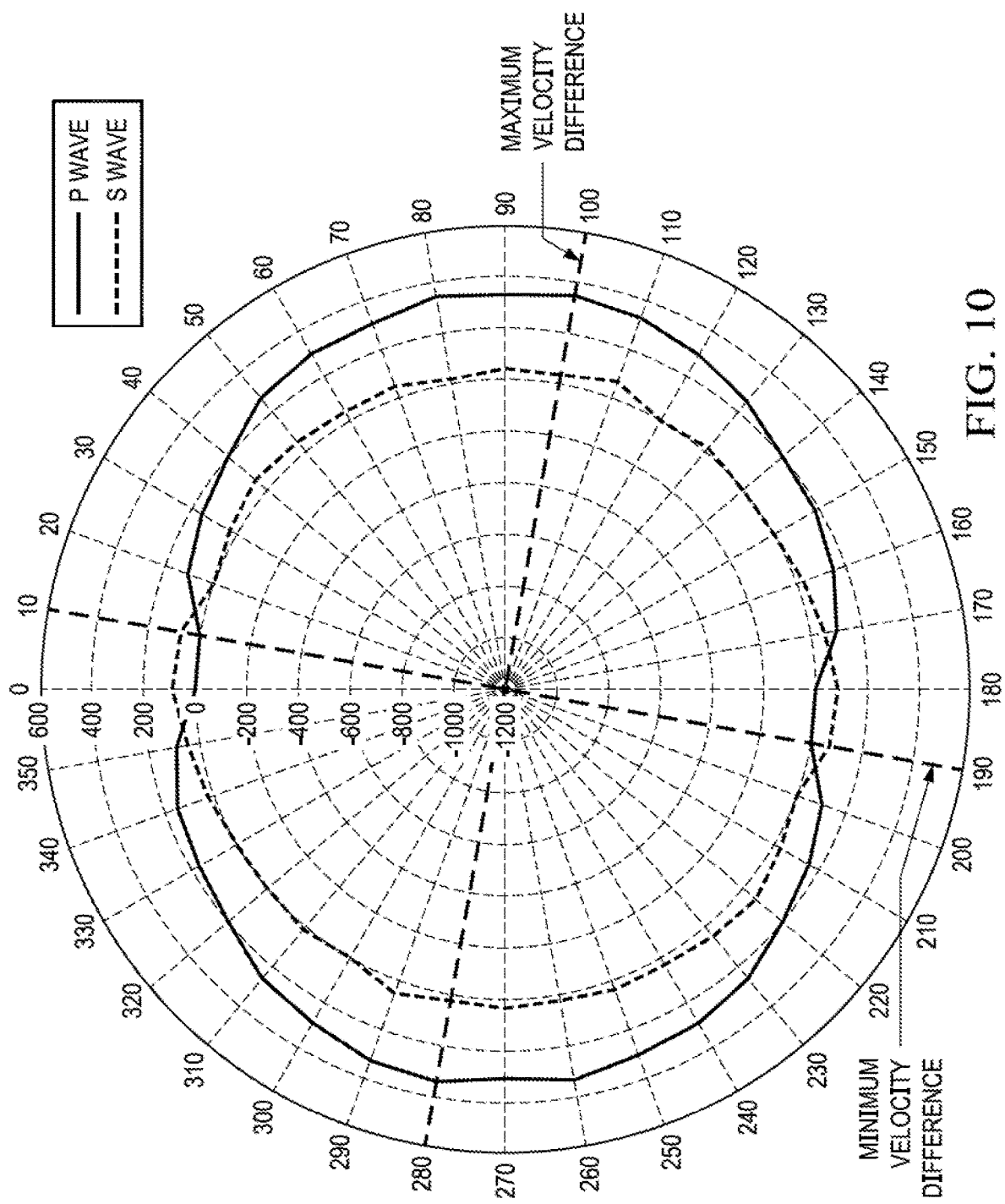

FIG. 10 plots the maximum P-wave orientation along N80° W from sample #8.

Figure 11:
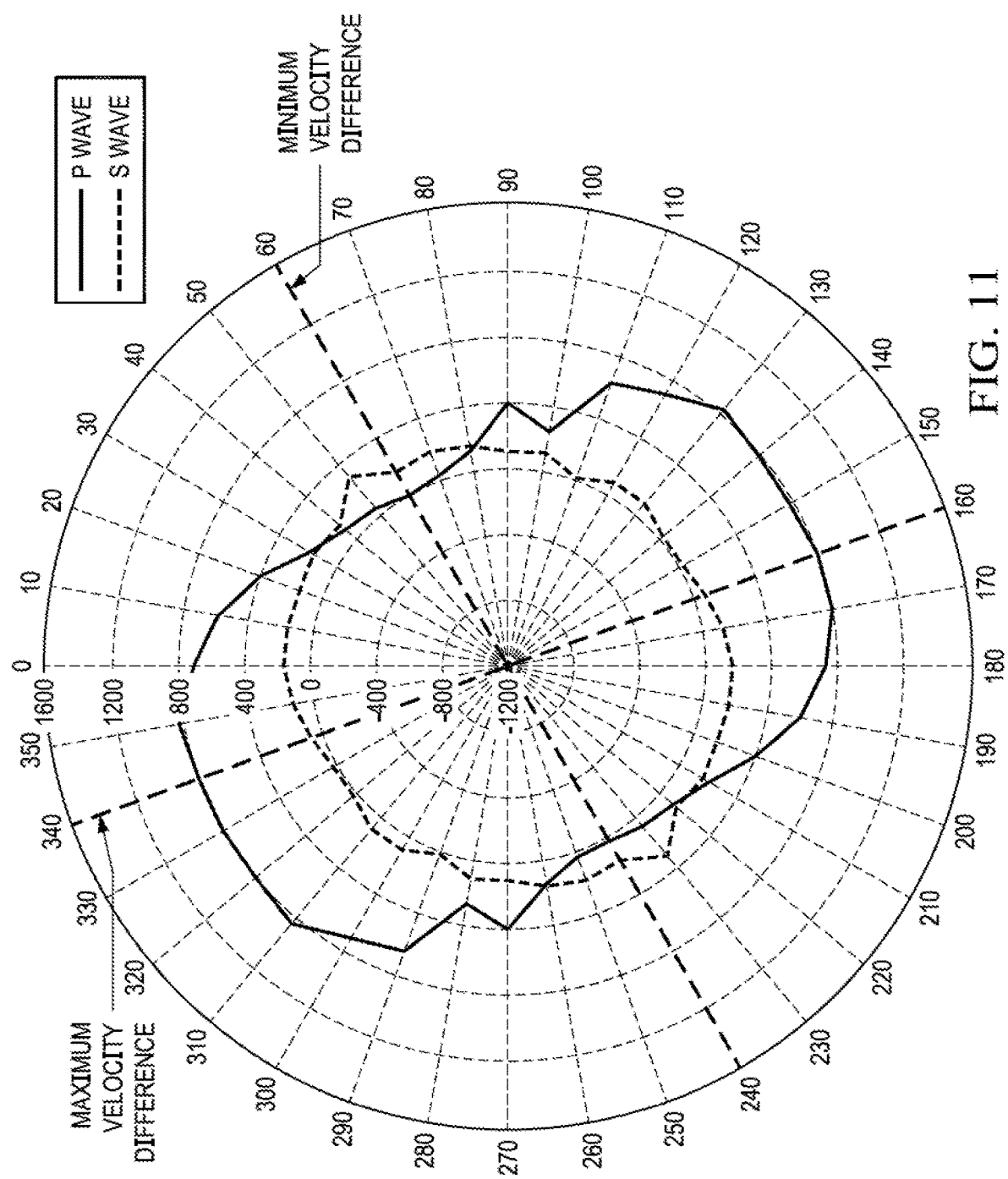

FIG. 11 plots the maximum P-wave orientation along N20° W from sample #9.

Figure 12:
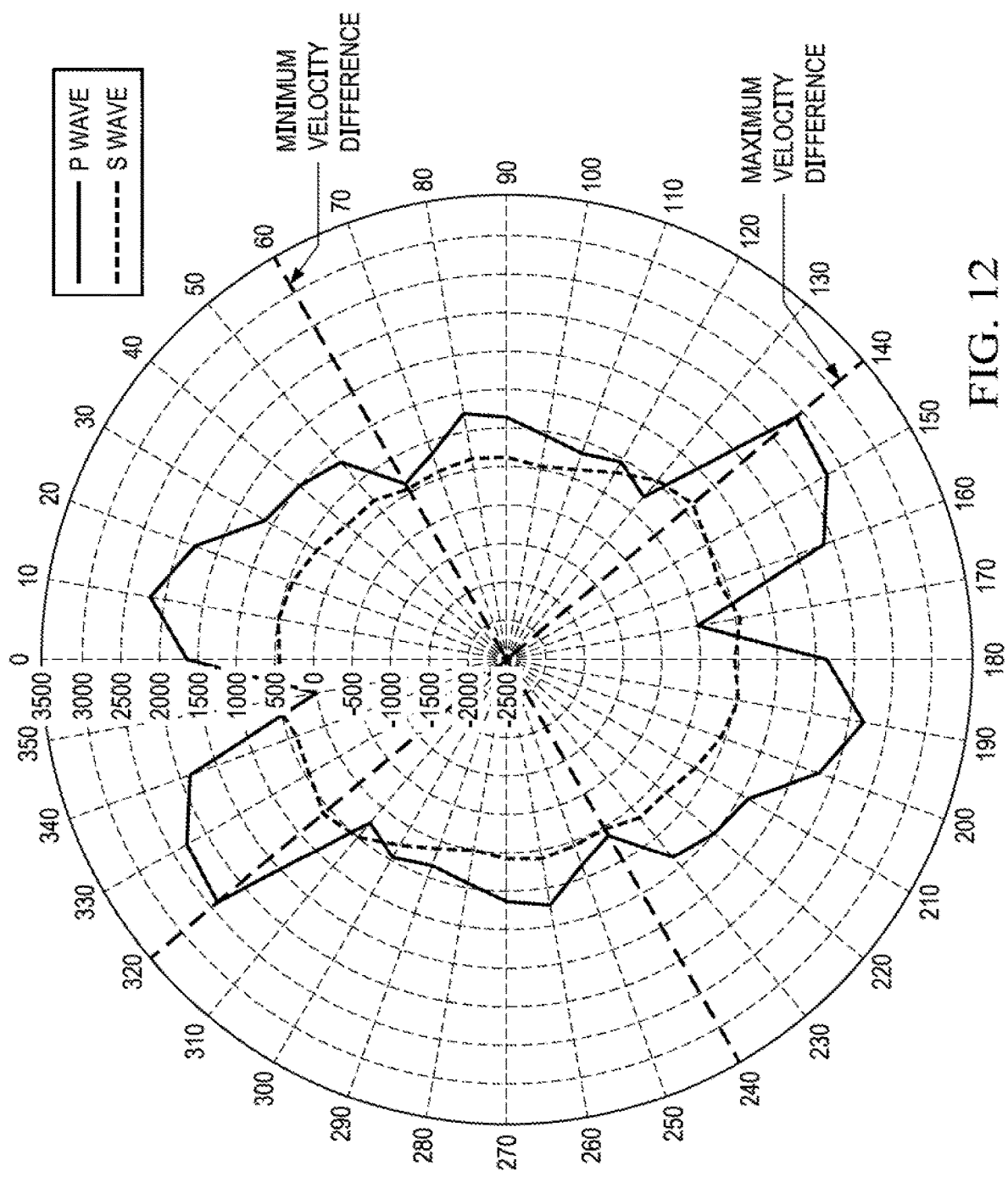

FIG. 12 plots the maximum P-wave orientation along N40° W from sample #10.

Figure 13:
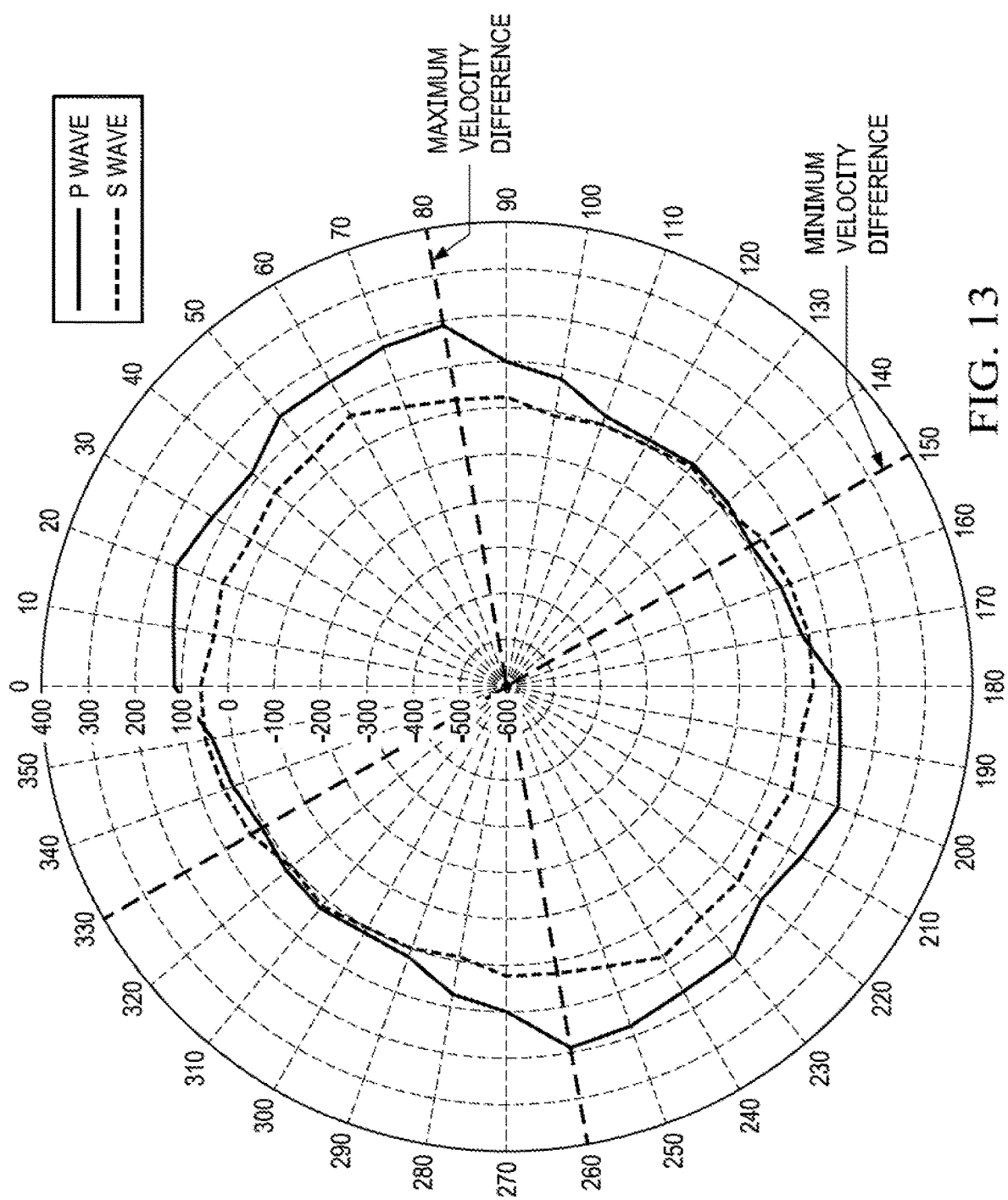

FIG. 13 plots the maximum P-wave orientation along N80° E from sample #12.

Figure 14:
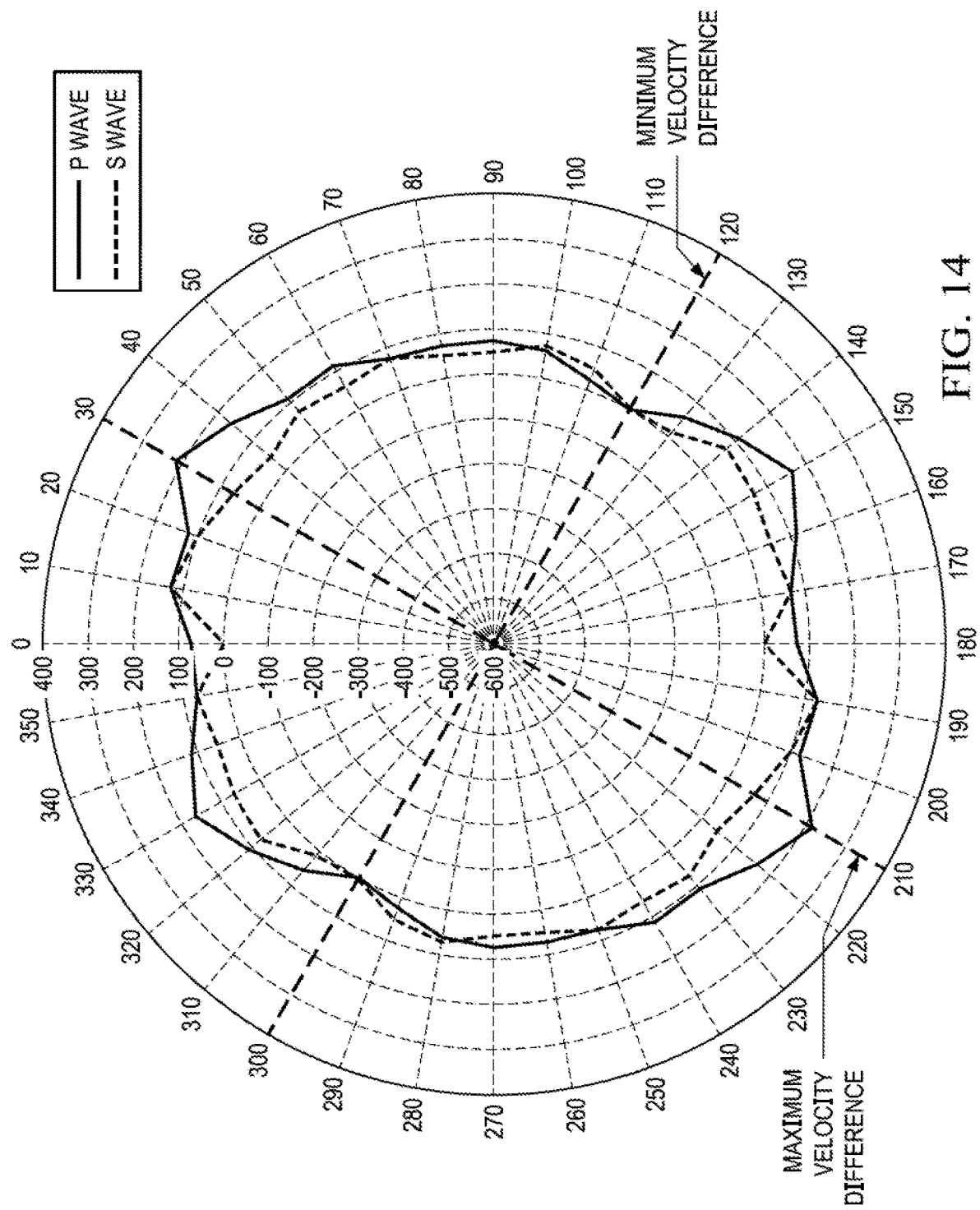

FIG. 14 plots the maximum P-wave orientation along N30° E from sample #14.

Figure 15:
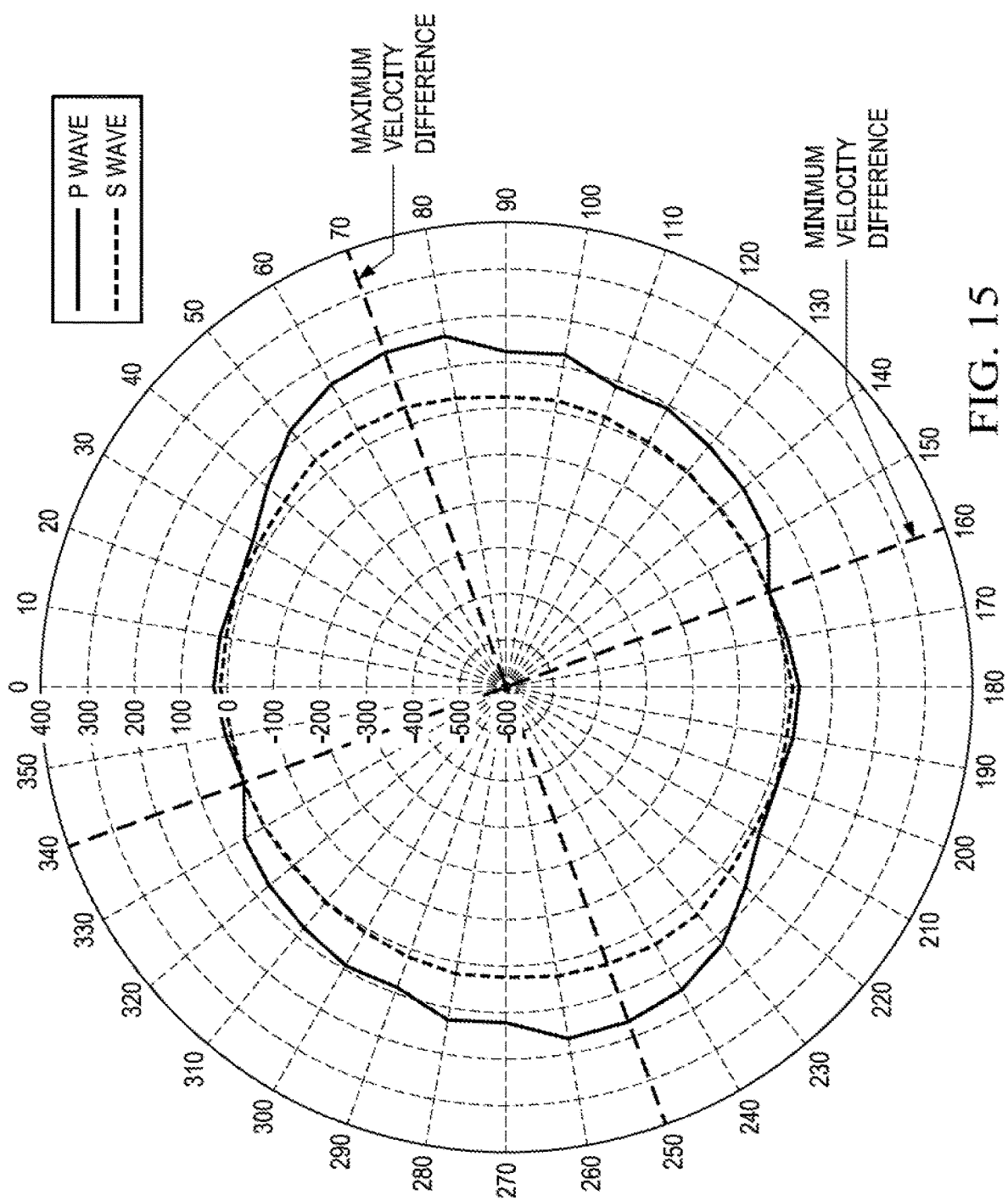

FIG. 15 plots the maximum P-wave orientation along N70° E from sample #15.

Figure 16:
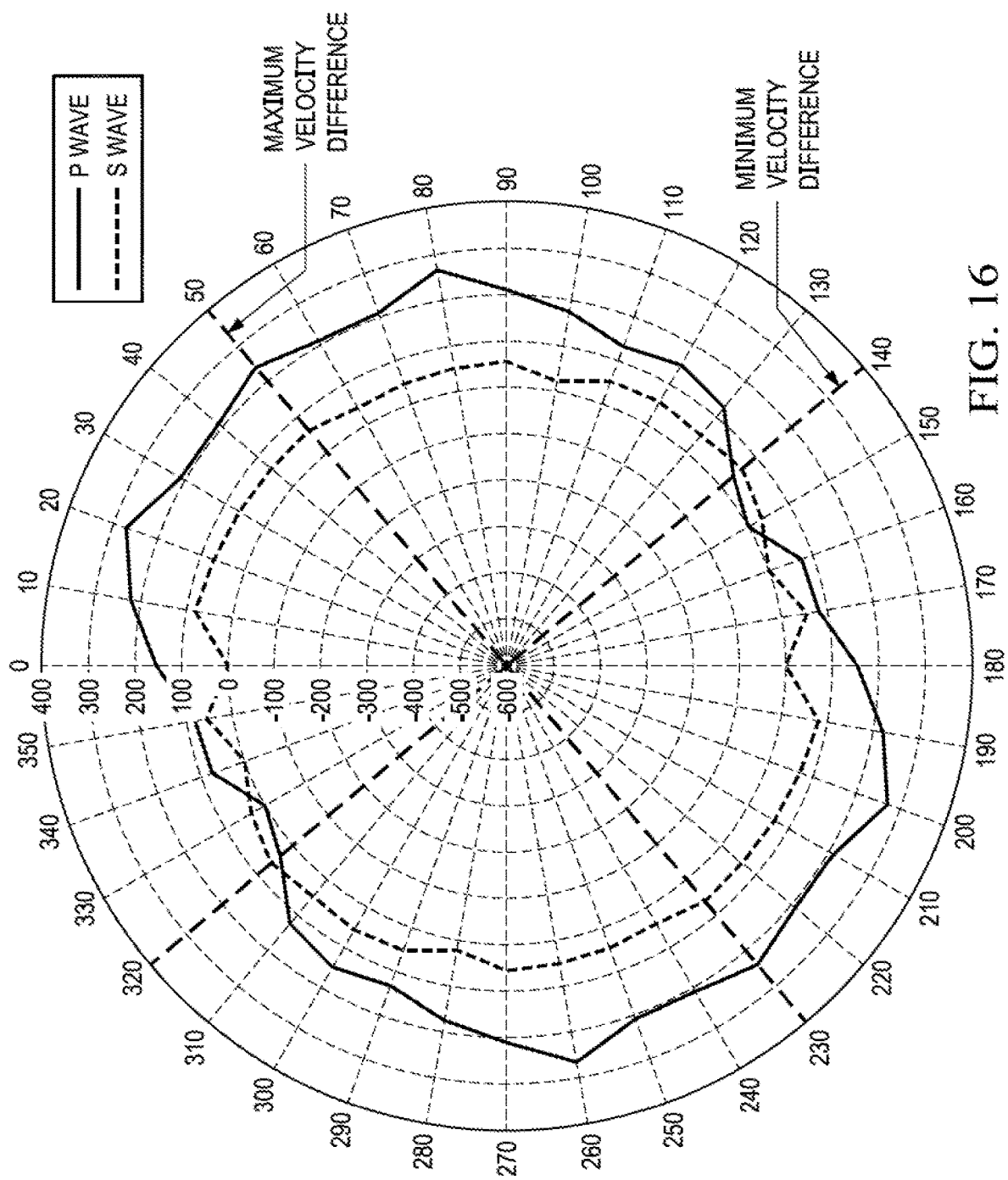

FIG. 16 shows the maximum P-wave orientation along N50° E from sample #16.

Figure 17:
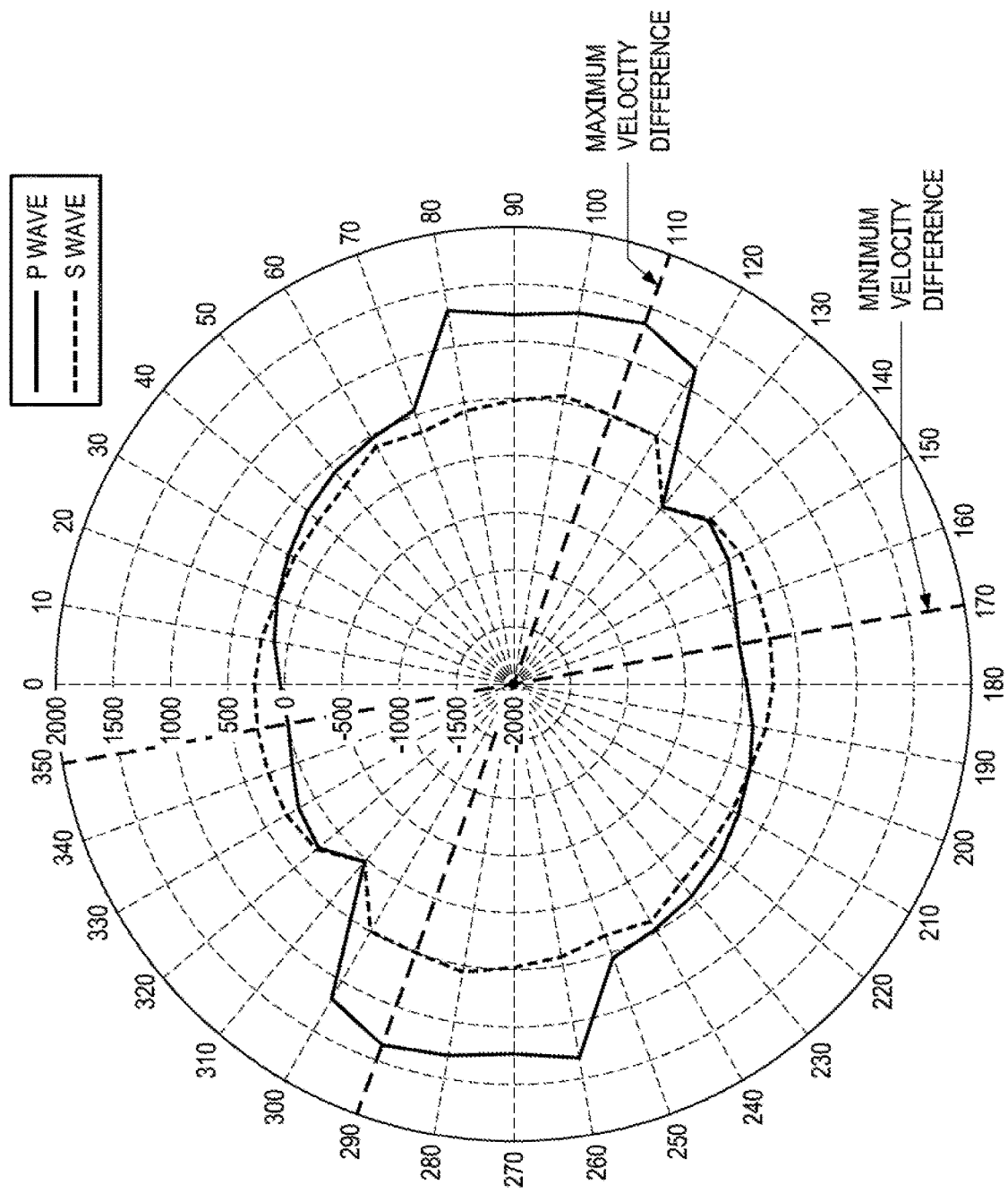

FIG. 17 shows the maximum P-wave orientation along N0° E from sample #18.

Figure 18:
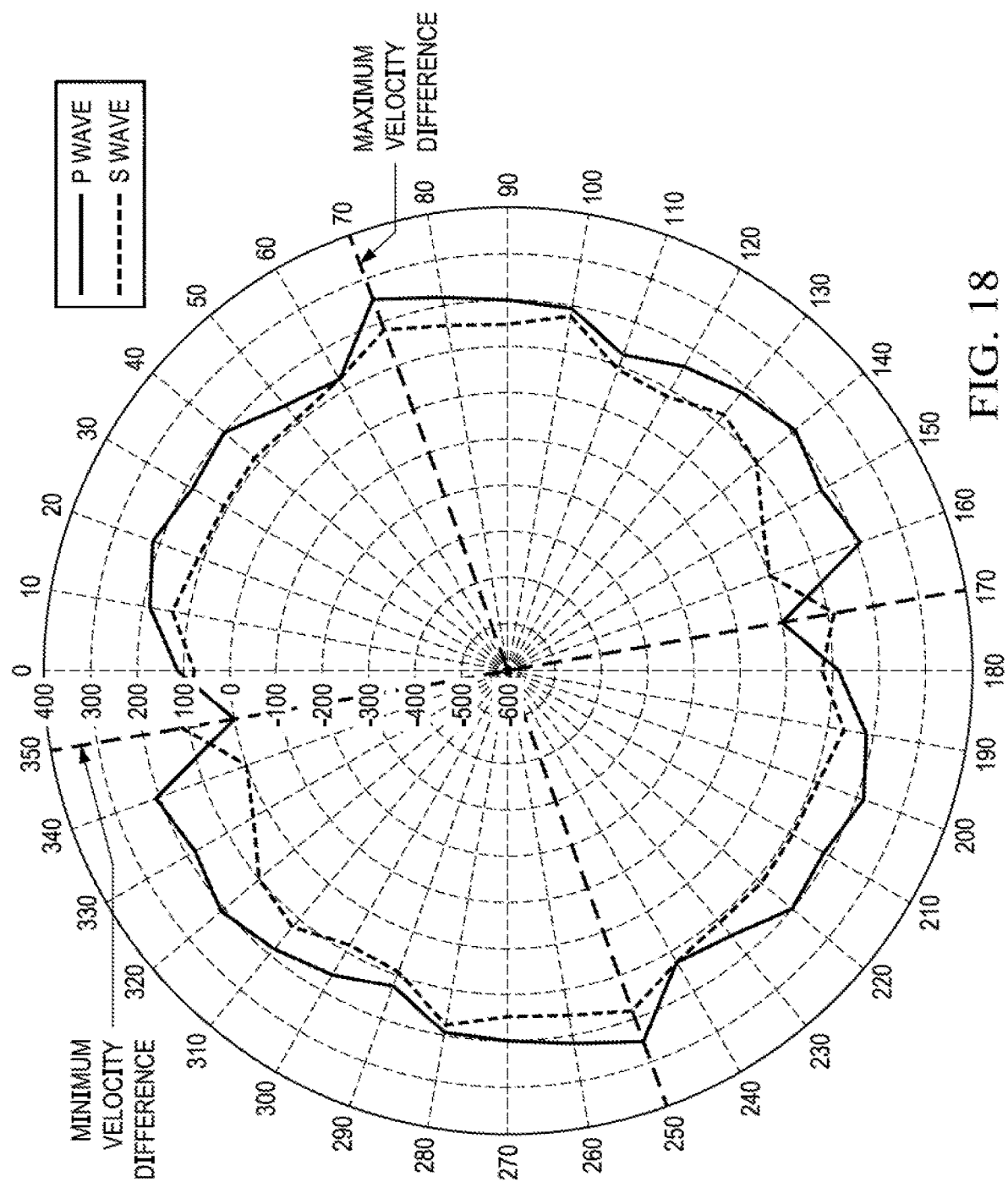

FIG. 18 shows the maximum P-wave orientation along N0° E from sample #19.

Figure 19:
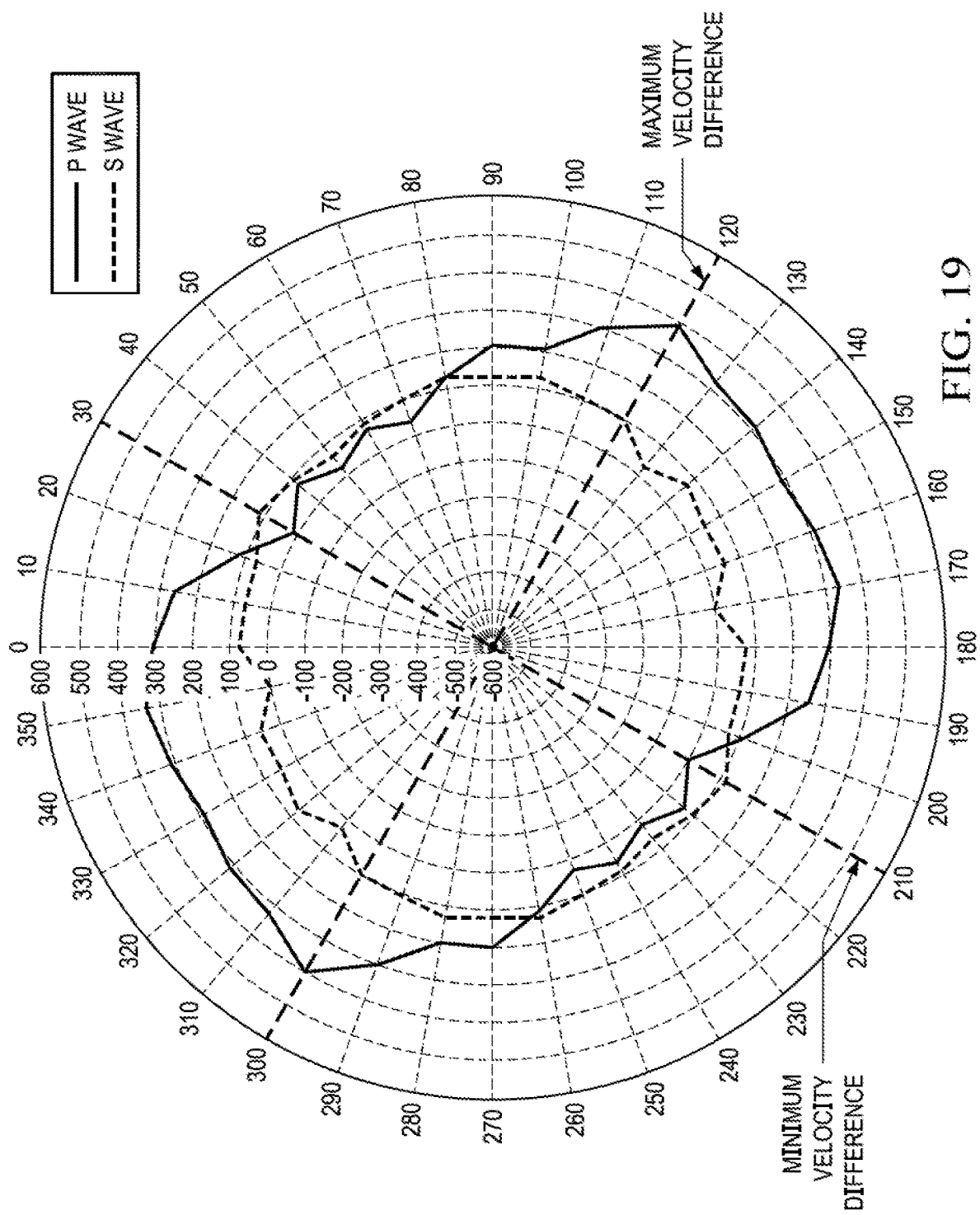

FIG. 19 shows the maximum P-wave orientation along N60° W from sample #20.

Figure 20:
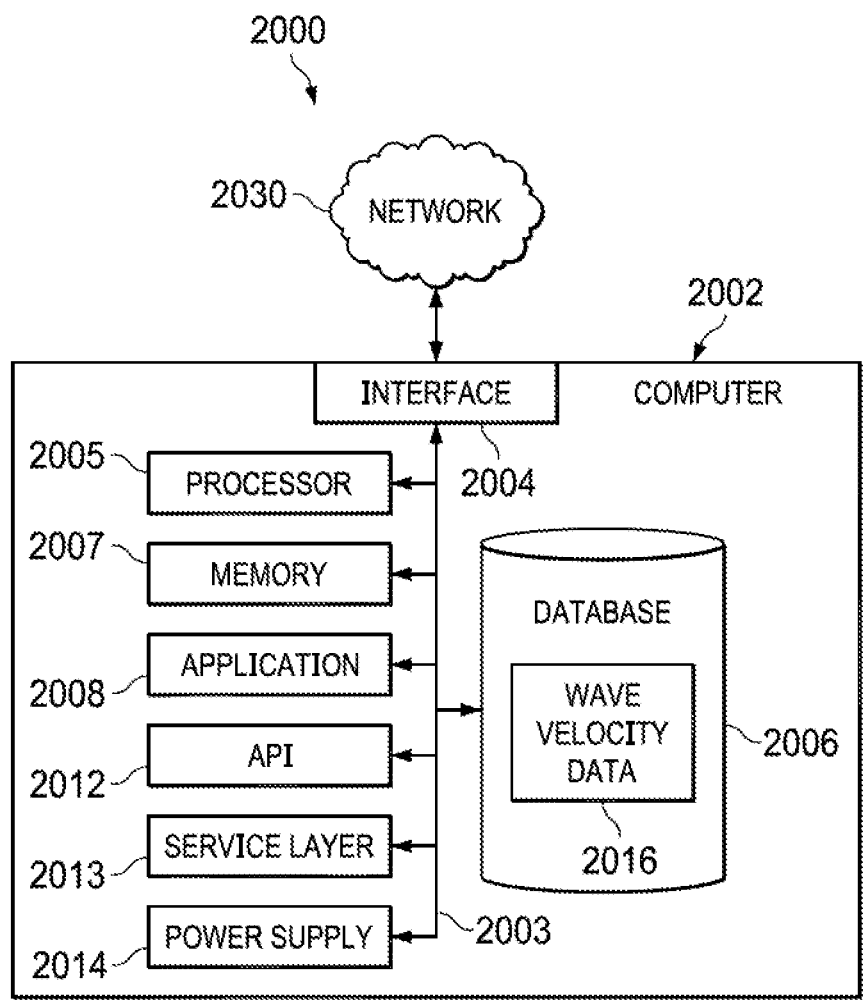
FIG. 20 is a block diagram illustrating an example computer system used to provide computational functionalities associated with described algorithms, methods, functions, processes, flows, and procedures as described in the present disclosure, according to some implementations of the present disclosure.

FIG. 20 is a block diagram of an example computer system 2000 used to provide computational functionalities associated with described algorithms, methods, functions, processes, flows, and procedures described in the present disclosure, according to some implementations of the present disclosure. The illustrated computer 2002 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 2002 can include input devices such as keypads, keyboards, and touch screens that can accept user information. Also, the computer 2002 can include output devices that can convey information associated with the operation of the computer 2002. The information can include digital data, visual data, audio information, or a combination of information. The information can be presented in a graphical user interface (UI) (or GUI).

The computer 2002 can serve in a role as a client, a network component, a server, a database, a persistency, or components of a computer system for performing the subject matter described in the present disclosure. The illustrated computer 2002 is communicably coupled with a network 2030. In some implementations, one or more components of the computer 2002 can be configured to operate within different environments, including cloud-computing-based environments, local environments, global environments, and combinations of environments.

At a high level, the computer 2002 is an electronic computing device operable to receive, transmit, process, store, and manage data and information associated with the described subject matter. According to some implementations, the computer 2002 can also include, or be communicably coupled with, an application server, an email server, a web server, a caching server, a streaming data server, or a combination of servers.

The computer 2002 can receive requests over network 2030 from a client application (for example, executing on another computer 2002). The computer 2002 can respond to the received requests by processing the received requests using software applications. Requests can also be sent to the computer 2002 from internal users (for example, from a command console), external (or third) parties, automated applications, entities, individuals, systems, and computers.

Each of the components of the computer 2002 can communicate using a system bus 2003. In some implementations, any or all of the components of the computer 2002, including hardware or software components, can interface with each other or the interface 2004 (or a combination of both), over the system bus 2003. Interfaces can use an application programming interface (API) 2012, a service layer 2013, or a combination of the API 2012 and service layer 2013. The API 2012 can include specifications for routines, data structures, and object classes. The API 2012 can be either computer-language independent or dependent. The API 2012 can refer to a complete interface, a single function, or a set of APIs.

The service layer 2013 can provide software services to the computer 2002 and other components (whether illustrated or not) that are communicably coupled to the computer 2002. The functionality of the computer 2002 can be accessible for all service consumers using this service layer. Software services, such as those provided by the service layer 2013, can provide reusable, defined functionalities through a defined interface. For example, the interface can be software written in JAVA, C++, or a language providing data in extensible markup language (XML) format. While illustrated as an integrated component of the computer 2002, in alternative implementations, the API 2012 or the service layer 2013 can be stand-alone components in relation to other components of the computer 2002 and other components communicably coupled to the computer 2002. Moreover, any or all parts of the API 2012 or the service layer 2013 can be implemented as child or sub-modules of another software module, enterprise application, or hardware module without departing from the scope of the present disclosure.

The computer 2002 includes an interface 2004. Although illustrated as a single interface 2004 in FIG. 20, two or more interfaces 2004 can be used according to particular needs, desires, or particular implementations of the computer 2002 and the described functionality. The interface 2004 can be used by the computer 2002 for communicating with other systems that are connected to the network 2030 (whether illustrated or not) in a distributed environment. Generally, the interface 2004 can include, or be implemented using, logic encoded in software or hardware (or a combination of software and hardware) operable to communicate with the network 2030. More specifically, the interface 2004 can include software supporting one or more communication protocols associated with communications. As such, the network 2030 or the hardware of the interface can be operable to communicate physical signals within and outside of the illustrated computer 2002.

The computer 2002 includes a processor 2005. Although illustrated as a single processor 2005 in FIG. 20, two or more processors 2005 can be used according to particular needs, desires, or particular implementations of the computer 2002 and the described functionality. Generally, the processor 2005 can execute instructions and can manipulate data to perform the operations of the computer 2002, including operations using algorithms, methods, functions, processes, flows, and procedures as described in the present disclosure.

The computer 2002 also includes a database 2006 that can hold data (for example, wave velocity data 2016) for the computer 2002 and other components connected to the network 2030 (whether illustrated or not). For example, database 2006 can be an in-memory, conventional, or a database storing data consistent with the present disclosure. In some implementations, database 2006 can be a combination of two or more different database types (for example, hybrid in-memory and conventional databases) according to particular needs, desires, or particular implementations of the computer 2002 and the described functionality. Although illustrated as a single database 2006 in FIG. 20, two or more databases (of the same, different, or combination of types) can be used according to particular needs, desires, or particular implementations of the computer 2002 and the described functionality. While database 2006 is illustrated as an internal component of the computer 2002, in alternative implementations, database 2006 can be external to the computer 2002.

The computer 2002 also includes a memory 2007 that can hold data for the computer 2002 or a combination of components connected to the network 2030 (whether illustrated or not). Memory 2007 can store any data consistent with the present disclosure. In some implementations, memory 2007 can be a combination of two or more different types of memory (for example, a combination of semiconductor and magnetic storage) according to particular needs, desires, or particular implementations of the computer 2002 and the described functionality. Although illustrated as a single memory 2007 in FIG. 20, two or more memories 2007 (of the same, different, or combination of types) can be used according to particular needs, desires, or particular implementations of the computer 2002 and the described functionality. While memory 2007 is illustrated as an internal component of the computer 2002, in alternative implementations, memory 2007 can be external to the computer 2002.

The application 2008 can be an algorithmic software engine providing functionality according to particular needs, desires, or particular implementations of the computer 2002 and the described functionality. For example, application 2008 can serve as one or more components, modules, or applications. Further, although illustrated as a single application 2008, the application 2008 can be implemented as multiple applications 2008 on the computer 2002. In addition, although illustrated as internal to the computer 2002, in alternative implementations, the application 2008 can be external to the computer 2002.

The computer 2002 can also include a power supply 2014. The power supply 2014 can include a rechargeable or non-rechargeable battery that can be configured to be either user- or non-user-replaceable. In some implementations, the power supply 2014 can include power-conversion and management circuits, including recharging, standby, and power management functionalities. In some implementations, the power-supply 2014 can include a power plug to allow the computer 2002 to be plugged into a wall socket or a power source to, for example, power the computer 2002 or recharge a rechargeable battery.

There can be any number of computers 2002 associated with, or external to, a computer system containing computer 2002, with each computer 2002 communicating over network 2030. Further, the terms "client," "user," and other appropriate terminology can be used interchangeably, as appropriate, without departing from the scope of the present disclosure. Moreover, the present disclosure contemplates that many users can use one computer 2002 and one user can use multiple computers 2002.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/–R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of the systems and methods have been described. Nevertheless, it will be understood that various modifications may be made without departing from the spirit and scope of this disclosure. Accordingly, other embodiments are within the scope of the following claims.

What is claimed is:

1. A method for determining a reservoir characteristic of a subsurface formation, the method comprising:
   receiving a first core taken from the subsurface formation;
   determining an acoustic wave velocity associated with each of a plurality of directions extending diametrically across the first core by:
      transmitting an ultrasonic wave through the first core along a first direction of the plurality of directions;
      receiving the transmitted ultrasonic wave;
      determining the acoustic wave velocity associated with the first direction based on an arrival time of the transmitted ultrasonic wave; and
      rotating the first core about a longitudinal axis of the first core from the first direction to a second direction of the plurality of directions;
   determining a normalized acoustic wave velocity for each of the plurality of directions based on a difference of the determined acoustic wave velocity associated with a respective direction minus a minimum acoustic wave velocity of the acoustic wave velocities for all directions of the plurality of directions; and
   determining the reservoir characteristic of the subsurface formation based on the determined normalized acoustic wave velocity associated with each of the plurality of directions.

2. The method of claim 1, wherein determining the reservoir characteristic of the subsurface formation comprises determining that the subsurface formation comprises rock with anisotropic physical properties based on the determined acoustic wave velocity associated with each of the plurality of directions.

3. The method of claim 1, further comprising receiving a plurality of additional cores and determining an acoustic wave velocity associated with each of a plurality of directions extending diametrically across each of the plurality of additional cores.

4. The method of claim 3, further comprising building a map of the reservoir characteristics of the subsurface formation using the determined acoustic wave velocities associated with the first core and the plurality of additional cores.

5. The method of claim 3, wherein the plurality of additional cores are taken from a single well.

6. The method of claim 3, wherein the plurality of additional cores are taken from multiple wells.

7. The method of claim 1, wherein the ultrasonic wave propagates through the first core as a P-wave.

8. The method of claim 1, wherein the ultrasonic wave propagates through the first core as an S-wave.

9. The method of claim 1, further comprising storing the determined acoustic wave velocity along the first direction in a database.

10. The method of claim 1, wherein rotating the first core about the longitudinal axis of the first core comprises rotating the first core in a 10 degree increment.

11. A method for determining a reservoir characteristic of a subsurface formation, the method comprising:
   receiving a first core taken from the subsurface formation;
   determining an acoustic wave velocity associated with each of a plurality of directions extending diametrically across the first core by:

transmitting an ultrasonic wave through the first core along a first direction of the plurality of directions;

receiving the transmitted ultrasonic wave;

determining the acoustic wave velocity associated with the first direction based on an arrival time of the transmitted ultrasonic wave; and rotating the first core about a longitudinal axis of the first core from the first direction to a second direction of the plurality of directions;

determining a normalized acoustic wave velocity for each of the plurality of directions based on a difference of each determined wave velocity associated with a respective direction minus a maximum wave velocity of the wave velocities for all directions of the plurality of directions; and determining the reservoir characteristic of the subsurface formation based on the determined normalized acoustic wave velocity associated with each of the plurality of directions.

12. The method of claim 11, wherein determining the reservoir characteristic of the subsurface formation comprises determining that the subsurface formation comprises rock with anisotropic physical properties based on the determined acoustic wave velocity associated with each of the plurality of directions.

13. The method of claim 11, further comprising receiving a plurality of additional cores and determining an acoustic wave velocity associated with each of a plurality of directions extending diametrically across each of the plurality of additional cores.

14. The method of claim 13, further comprising building a map of the reservoir characteristics of the subsurface formation using the determined acoustic wave velocities associated with the first core and the plurality of additional cores.

15. The method of claim 13, wherein the plurality of additional cores are taken from a single well.

16. The method of claim 13, wherein the plurality of additional cores are taken from multiple wells.

17. The method of claim 11, wherein the ultrasonic wave propagates through the first core as a P-wave.

18. The method of claim 11, wherein the ultrasonic wave propagates through the first core as a S-wave.

19. The method of claim 11, further comprising storing the determined acoustic wave velocity along the first direction in a database.

20. The method of claim 11, wherein rotating the first core about the longitudinal axis of the first core comprises rotating the first core in a 10 degree increment.

* * * * *